(12) United States Patent
Peterson et al.

(10) Patent No.: US 9,439,700 B2
(45) Date of Patent: Sep. 13, 2016

(54) BONE ANCHOR WITH LOCKING CAP AND METHOD OF SPINAL FIXATION

(71) Applicant: DePuy Synthes Products, Inc., Raynham, MA (US)

(72) Inventors: Joseph Peterson, Malvern, PA (US); Dennis Chien, West Chester, PA (US); Thomas Keyer, West Chester, PA (US); Edward McShane, Collegeville, PA (US); Joseph Capozzoli, Mount Laurel, NJ (US); Pascal Hauri, Sion (CH); Scott Kramer, West Chester, PA (US); David Schindler, Lecanto, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 115 days.

(21) Appl. No.: 14/275,728

(22) Filed: May 12, 2014

(65) Prior Publication Data
US 2014/0249590 A1 Sep. 4, 2014

Related U.S. Application Data

(63) Continuation of application No. 13/524,371, filed on Jun. 15, 2012, now Pat. No. 8,740,946, which is a continuation of application No. 11/912,595, filed as application No. PCT/US2006/015692 on Apr. 25, 2006, now Pat. No. 8,221,472.

(60) Provisional application No. 60/674,877, filed on Apr. 25, 2005.

(51) Int. Cl.
*A61B 17/70* (2006.01)
*A61B 17/86* (2006.01)

(52) U.S. Cl.
CPC ....... *A61B 17/8605* (2013.01); *A61B 17/7032* (2013.01); *A61B 17/7037* (2013.01)

(58) Field of Classification Search
CPC .............. A61B 17/70; A61B 17/7032; A61B 17/7034; A61B 17/7035
USPC ................................. 606/264–275, 300–321
See application file for complete search history.

(56) References Cited

U.S. PATENT DOCUMENTS 4,950,269 A   8/1990 Gaines, Jr.
5,207,678 A   5/1993 Harms et al.
(Continued)

FOREIGN PATENT DOCUMENTS

CN   1433740 A   8/2003
DE   19509332 C1  8/1996
(Continued)

OTHER PUBLICATIONS

International Preliminary Report of Patentability with Written Opinion from the International Bureau for International Application No. PCT/US2006/015692 dated Oct. 30, 2007.
(Continued)

*Primary Examiner* — Ellen C Hammond
*Assistant Examiner* — Christina Negrellirodrigue
(74) *Attorney, Agent, or Firm* — Nutter McClennen & Fish LLP

(57) ABSTRACT

A bone anchor (100) for attaching a rod (108) to a bone has an anchor member (106) for attachment to the bone and an anchor head (104) having a U-shaped opening for receiving the rod. The bone anchor also includes a locking cap (102) that has a main body (900) and a set screw (1000). Advantageously, in one embodiment the locking cap preferably is designed such that a single tool can be used to lock the locking cap in place on the anchor body preferably with a 90° turn and preferably then drive the set screw to clamp the rod. The locking cap also preferably non-threadingly engages the anchor body. The anchor body preferably has an inclined surface on its top surface which elastically deflects extending tabs on the main body to secure the locking cap to the anchor body. A method of implantation and assembly of the bone anchor are also described.

20 Claims, 15 Drawing Sheets

(56) References Cited

U.S. PATENT DOCUMENTS

| | | |
|---|---|---|
| 5,257,993 A | 11/1993 | Asher et al. |
| 5,304,179 A | 4/1994 | Wagner |
| 5,346,493 A | 9/1994 | Stahurski et al. |
| 5,474,555 A | 12/1995 | Puno et al. |
| 5,476,464 A | 12/1995 | Metz-Stavenhagen et al. |
| 5,586,984 A | 12/1996 | Errico et al. |
| 5,669,911 A | 9/1997 | Errico et al. |
| 5,672,176 A | 9/1997 | Biedermann et al. |
| 5,683,390 A | 11/1997 | Metz-Stavenhagen et al. |
| 5,690,630 A | 11/1997 | Errico et al. |
| 5,797,911 A | 8/1998 | Sherman et al. |
| 5,863,293 A | 1/1999 | Richelsoph |
| 5,879,350 A | 3/1999 | Sherman et al. |
| 5,885,286 A | 3/1999 | Sherman et al. |
| 5,964,760 A | 10/1999 | Richelsoph |
| 6,010,503 A | 1/2000 | Richelsoph et al. |
| 6,053,917 A | 4/2000 | Sherman et al. |
| 6,077,262 A | 6/2000 | Schlapfer et al. |
| 6,090,111 A | 7/2000 | Nichols |
| 6,132,432 A | 10/2000 | Richelsoph |
| 6,248,105 B1 | 6/2001 | Schlapfer et al. |
| 6,261,287 B1 | 7/2001 | Metz-Stavenhagen |
| 6,280,442 B1 | 8/2001 | Barker et al. |
| 6,302,888 B1 | 10/2001 | Mellinger et al. |
| 6,355,040 B1 | 3/2002 | Richelsoph et al. |
| 6,402,752 B2 | 6/2002 | Schaffler-Wachter et al. |
| 6,478,797 B1 | 11/2002 | Paul |
| 6,485,491 B1 | 11/2002 | Farris et al. |
| 6,485,492 B1 | 11/2002 | Halm et al. |
| 6,488,681 B2 | 12/2002 | Martin et al. |
| 6,537,276 B2 | 3/2003 | Metz-Stavenhagen et al. |
| 6,540,749 B2 | 4/2003 | Schafer et al. |
| 6,565,565 B1 | 5/2003 | Yuan et al. |
| 6,565,566 B1 | 5/2003 | Wagner et al. |
| 6,585,737 B1 | 7/2003 | Baccelli et al. |
| 6,613,050 B1 | 9/2003 | Wagner et al. |
| 6,652,526 B1 | 11/2003 | Arafiles |
| 6,660,004 B2 | 12/2003 | Barker et al. |
| 6,740,086 B2 | 5/2004 | Richelsoph |
| 6,755,829 B1 | 6/2004 | Bono et al. |
| 6,783,527 B2 | 8/2004 | Drewry et al. |
| 6,786,903 B2 | 9/2004 | Lin |
| 6,786,908 B2 | 9/2004 | Hover et al. |
| 6,843,791 B2 | 1/2005 | Serhan |
| 6,858,030 B2 | 2/2005 | Martin et al. |
| 6,869,433 B2 | 3/2005 | Glascott |
| 6,896,677 B1 * | 5/2005 | Lin ............................ 606/266 |
| 6,918,911 B2 | 7/2005 | Biedermann et al. |
| 7,018,379 B2 | 3/2006 | Drewry et al. |
| 7,081,117 B2 | 7/2006 | Bono et al. |
| 7,128,743 B2 | 10/2006 | Metz-Stavenhagen |
| 7,141,051 B2 * | 11/2006 | Janowski ............ A61B 17/7037 606/272 |
| 7,214,245 B1 | 5/2007 | Marcolongo et al. |
| 7,250,052 B2 | 7/2007 | Landry et al. |
| 7,294,128 B2 | 11/2007 | Alleyne et al. |
| 7,811,310 B2 * | 10/2010 | Baker ................ A61B 17/7032 606/267 |
| 8,162,989 B2 | 4/2012 | Khalili |
| 8,221,472 B2 | 7/2012 | Peterson et al. |
| 8,475,495 B2 | 7/2013 | Iott et al. |
| 8,740,946 B2 | 6/2014 | Peterson et al. |
| 2002/0026193 A1 | 2/2002 | Barker et al. |
| 2002/0120272 A1 | 8/2002 | Yuan et al. |
| 2003/0100904 A1* | 5/2003 | Biedermann ................ 606/73 |
| 2003/0125742 A1 | 7/2003 | Yuan et al. |
| 2003/0187433 A1 | 10/2003 | Lin |
| 2003/0187434 A1 | 10/2003 | Lin |
| 2004/0138662 A1 | 7/2004 | Landry et al. |
| 2005/0033296 A1* | 2/2005 | Bono et al. ..................... 606/61 |
| 2005/0187548 A1 | 8/2005 | Butler et al. |
| 2008/0294202 A1 | 11/2008 | Peterson et al. |
| 2012/0253409 A1 | 10/2012 | Peterson et al. |

FOREIGN PATENT DOCUMENTS

| | | |
|---|---|---|
| EP | 836835 A2 | 4/1998 |
| EP | 1210914 A1 | 6/2002 |
| EP | 1354563 A2 | 10/2003 |
| EP | 1388323 A1 | 2/2004 |
| WO | 9639972 A1 | 12/1996 |
| WO | 9852482 A1 | 11/1998 |
| WO | 00/27297 A1 | 5/2000 |
| WO | 03096916 A1 | 11/2003 |
| WO | 2004018306 A2 | 3/2004 |
| WO | 2004032774 A1 | 4/2004 |
| WO | 2006116437 A2 | 11/2006 |

OTHER PUBLICATIONS

International Search Report from the European Patent Office for International Application No. PCT/US2006/015692 dated Dec. 12, 2006 andpublished as WO 2006/116437A3.

Non-Final Office Action dated Oct. 27, 2011 issued in parent U.S. Appl. No. 11/912,595.

U.S. Appl. No. 11/912,595, filed May 21, 2008, Bone Anchor With Locking Cap and Method of Spinal Fixation.

U.S. Appl. No. 13/524,371, filed Jun. 15, 2012, Bone Anchor With Locking Cap and Method of Spinal Fixation.

U.S. Appl. No. 14/246,358, filed Apr. 7, 2014, Bone Anchor With Locking Cap and Method of Spinal Fixation.

Chinese Office Action for Application No. 200680021866.4 issued Feb. 27, 2009 (11 pages).

* cited by examiner

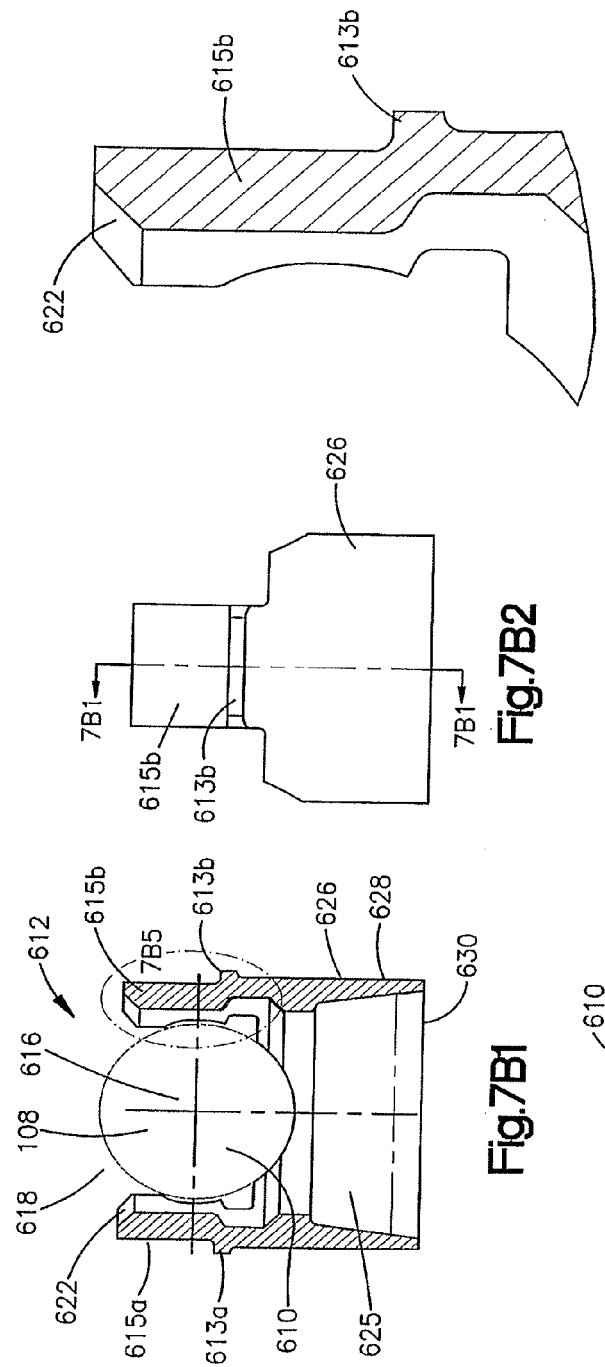

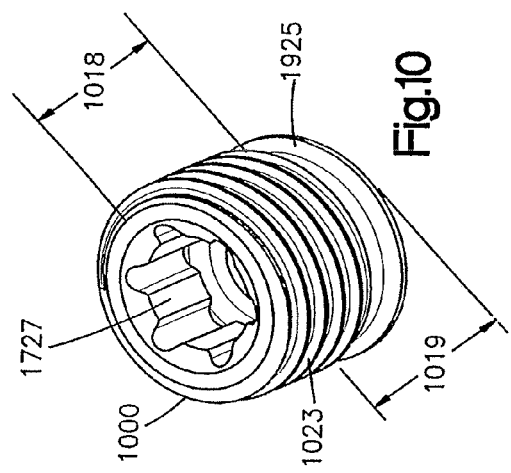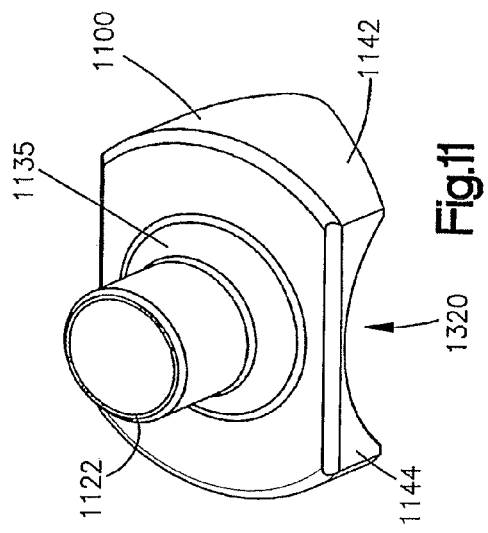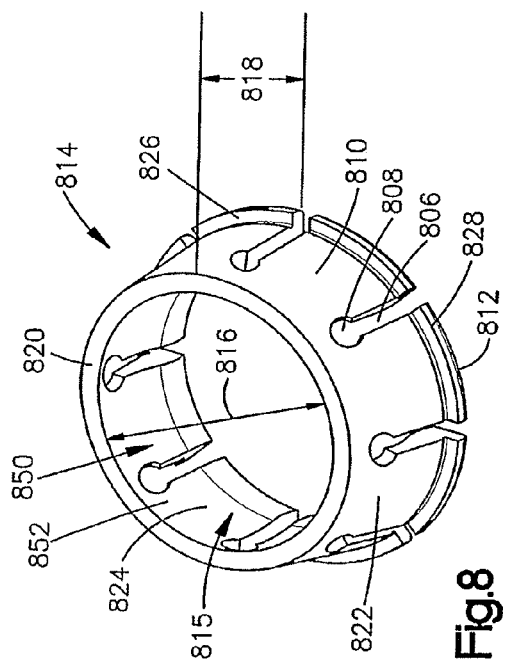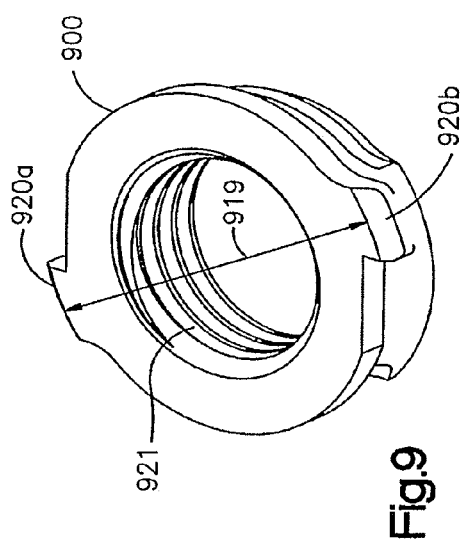

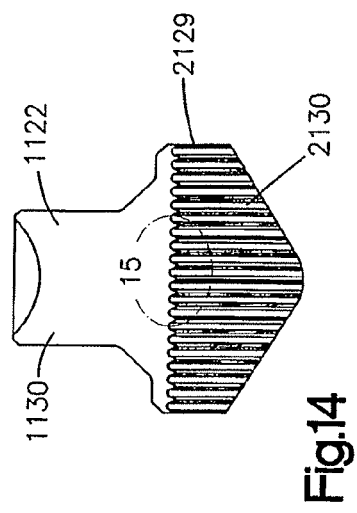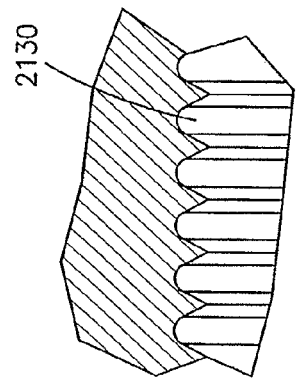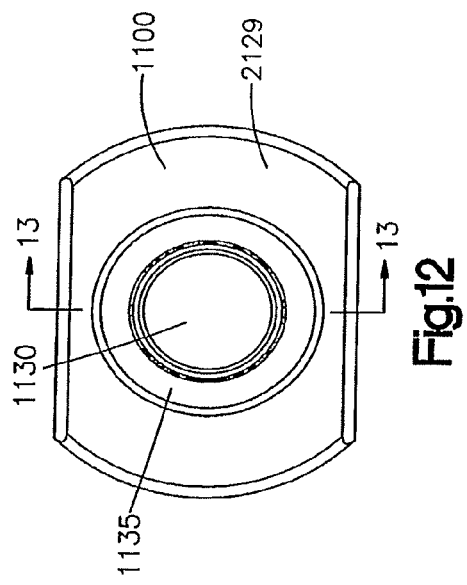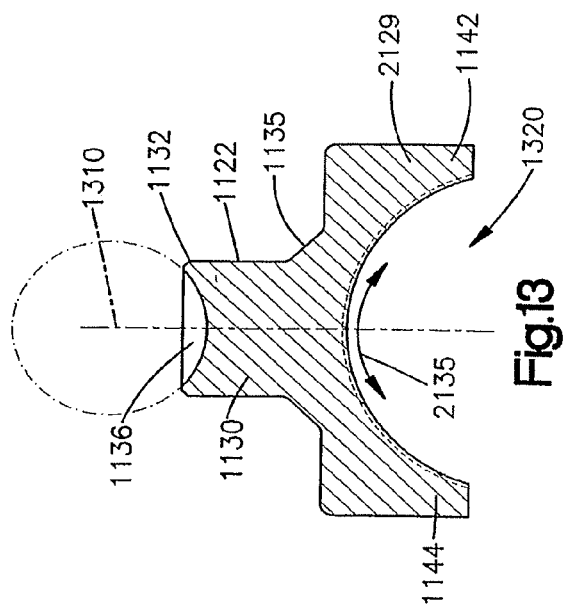

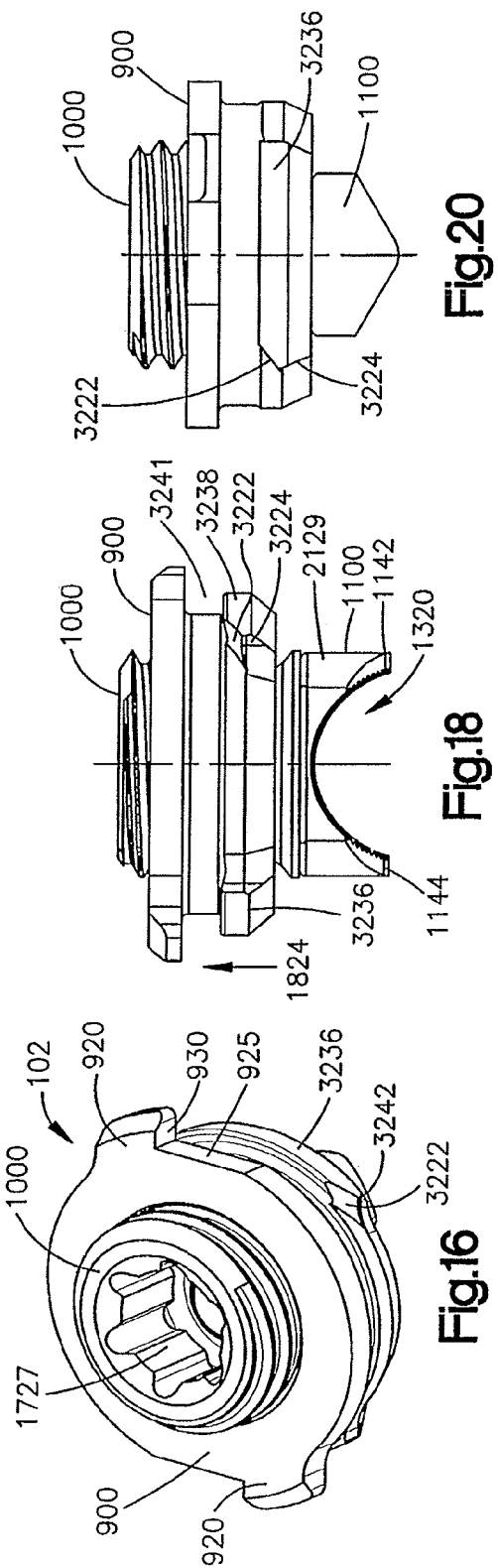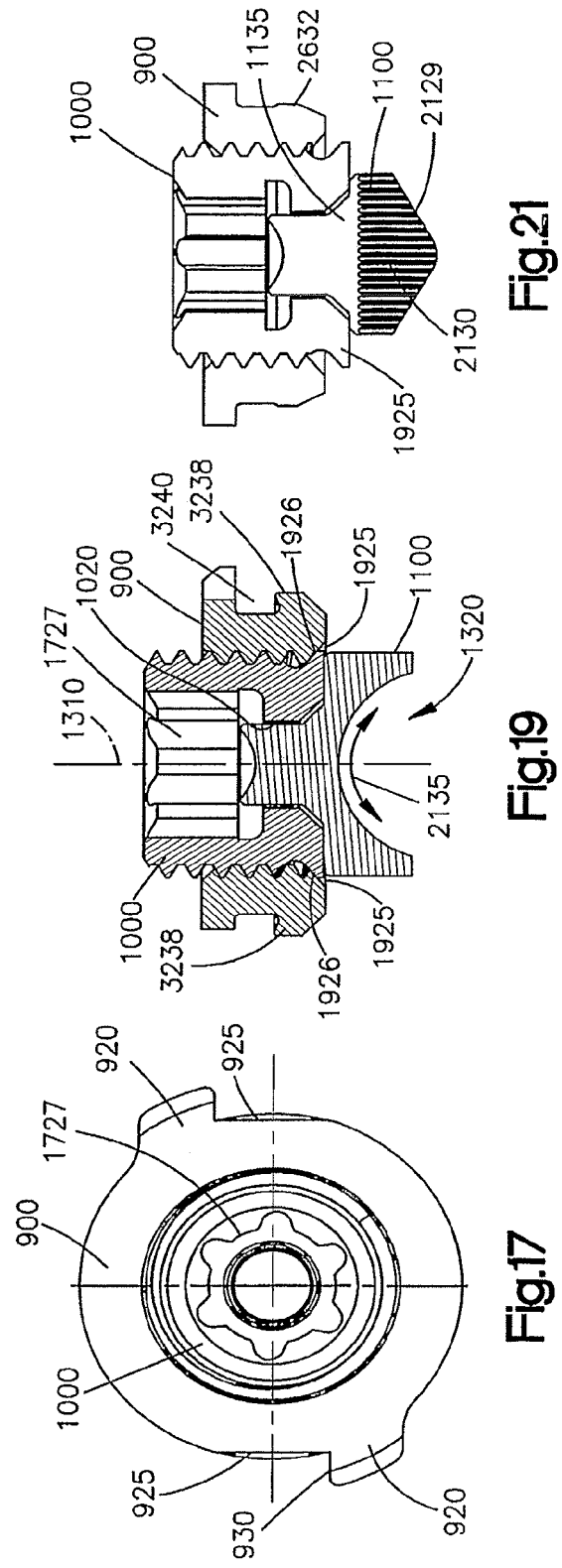

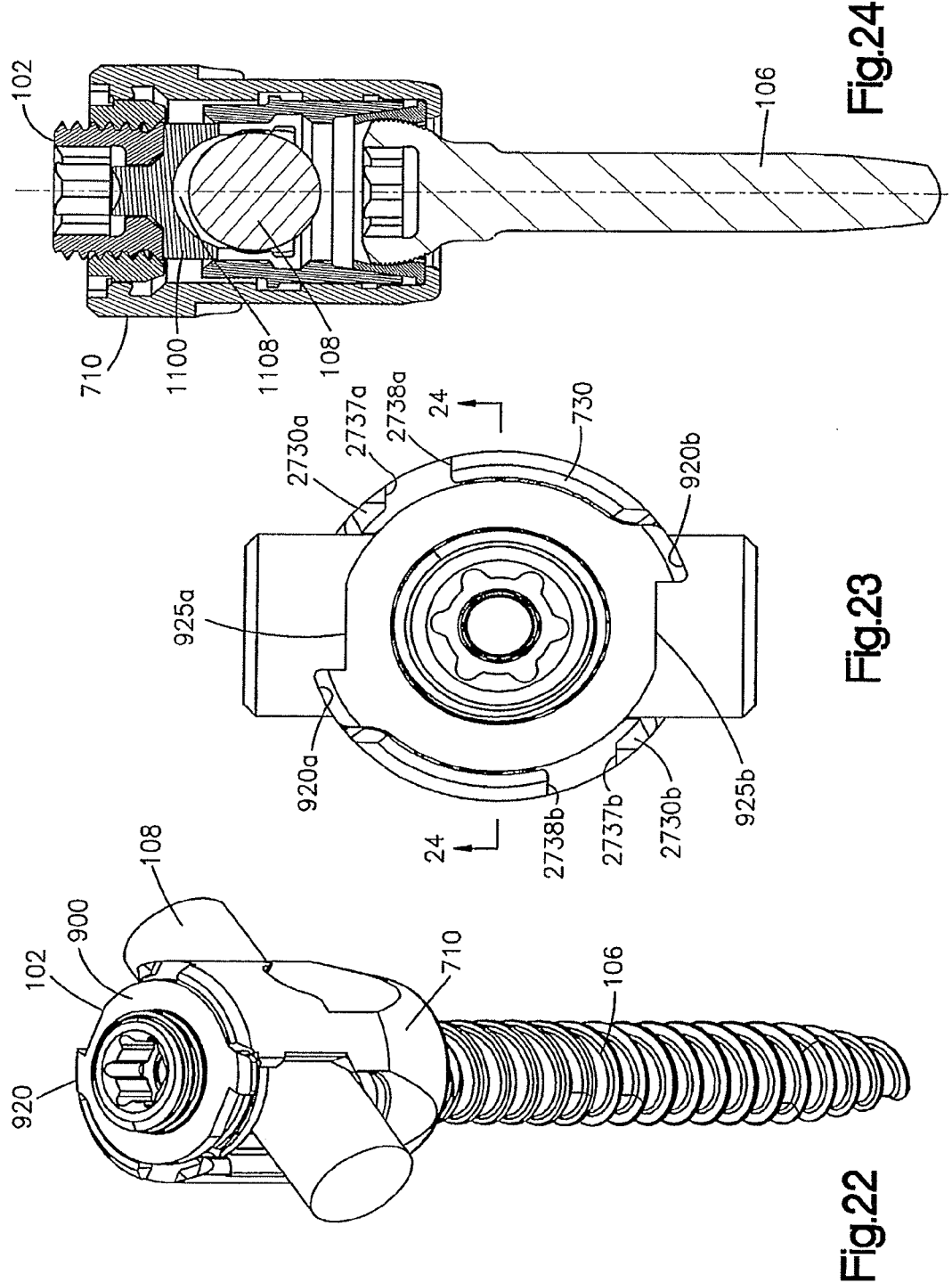

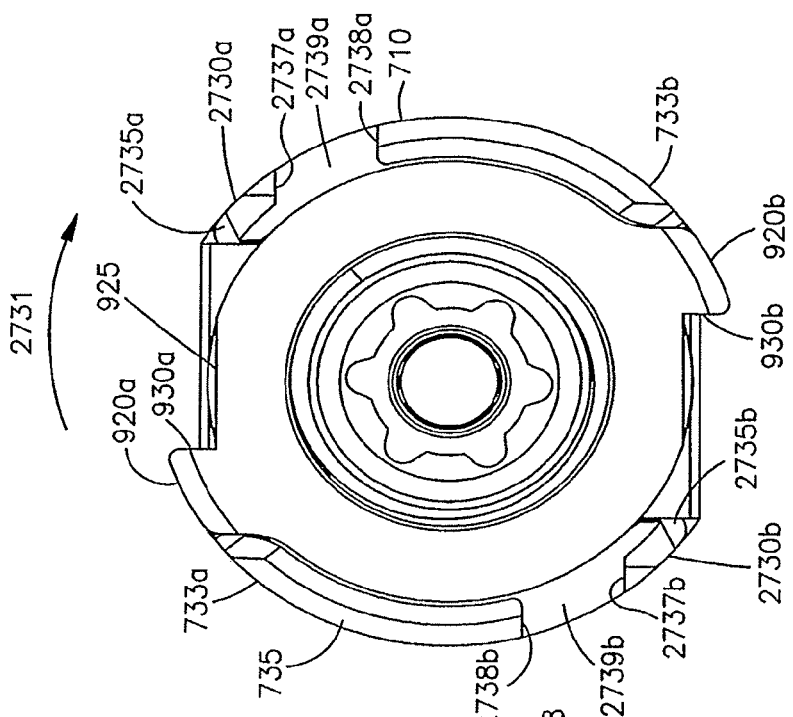
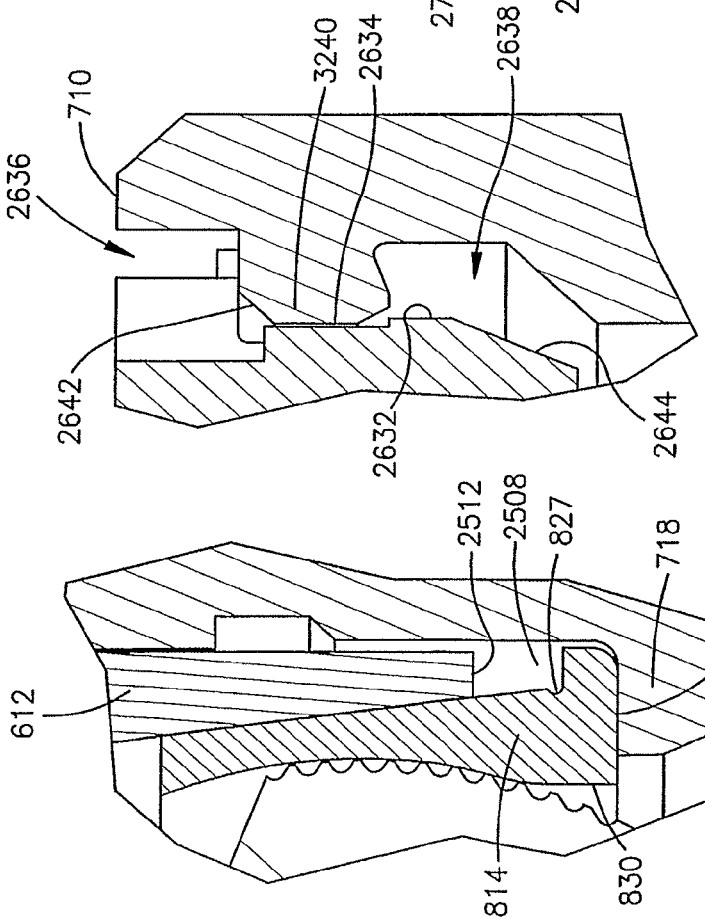

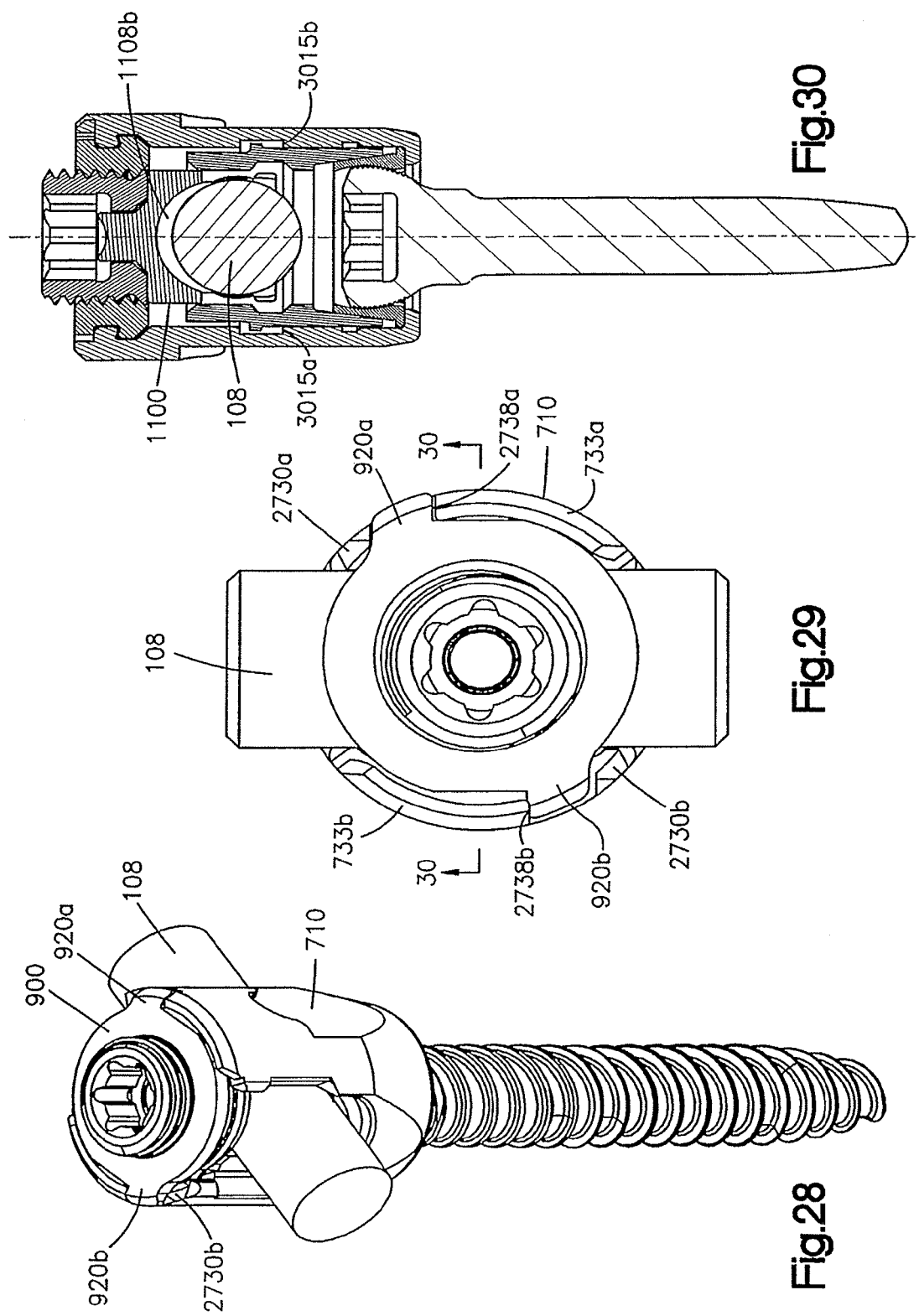

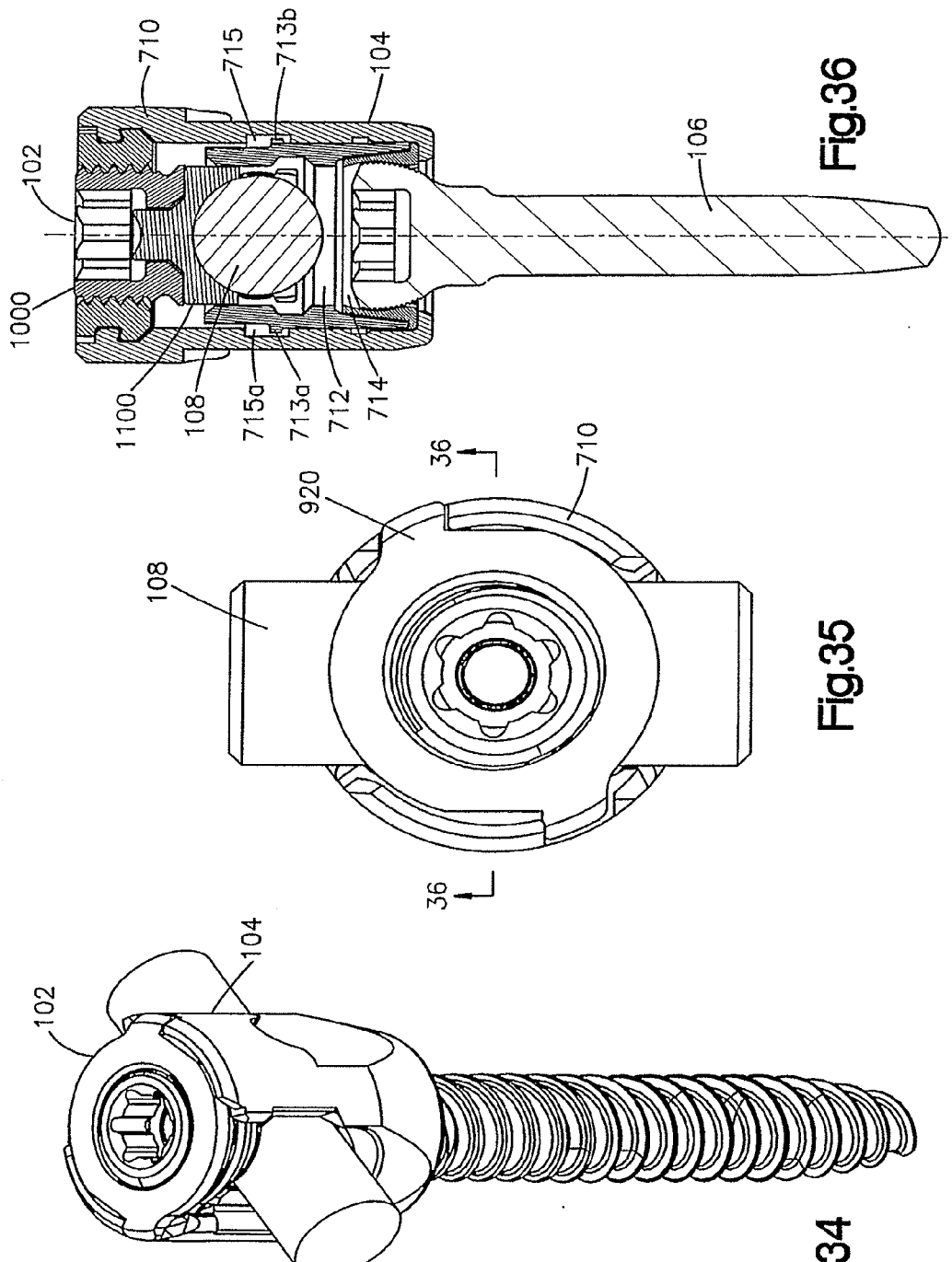

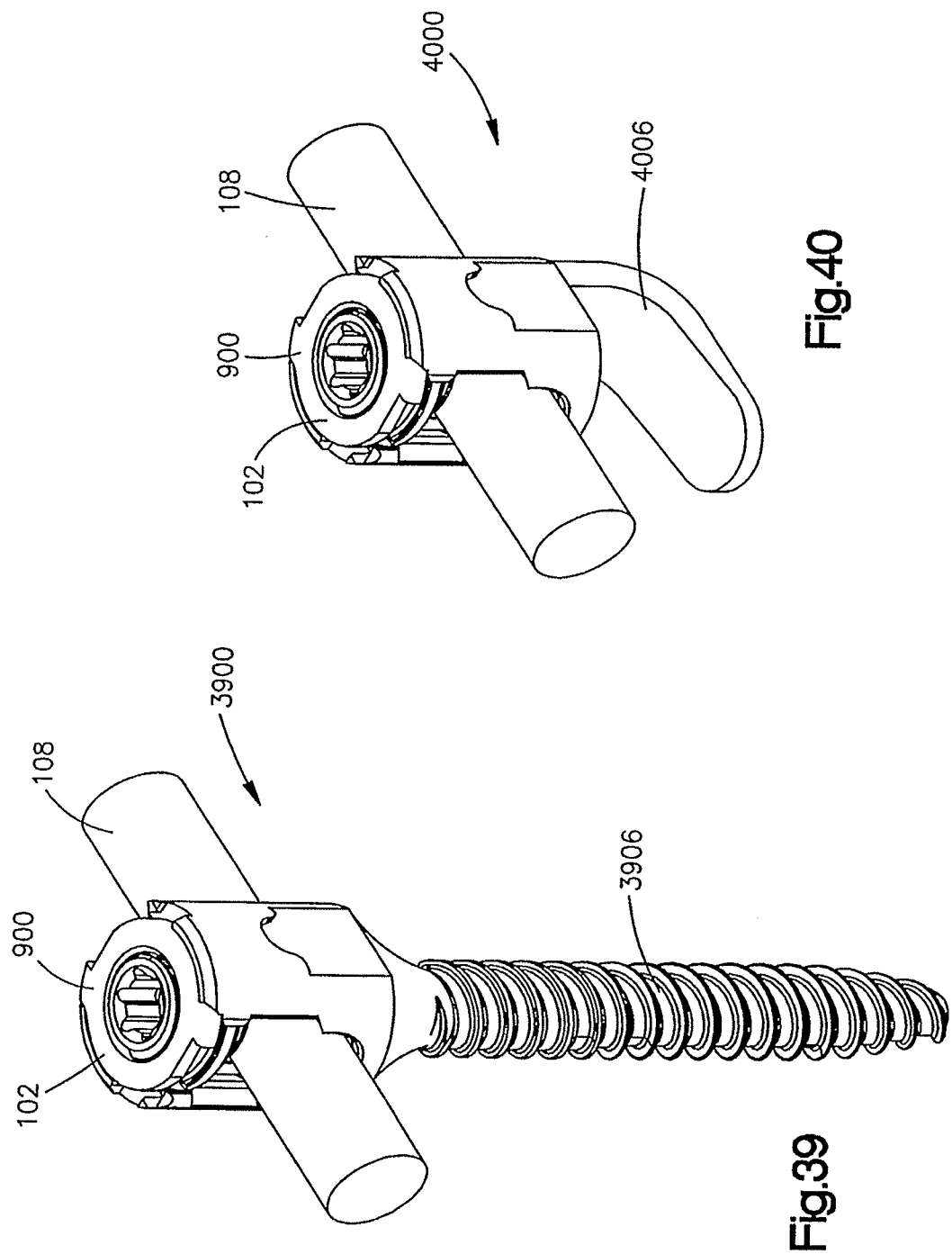

BONE ANCHOR WITH LOCKING CAP AND METHOD OF SPINAL FIXATION

CROSS-REFERENCE TO RELATED APPLICATIONS

This application is a continuation of U.S. patent application Ser. No. 13/524,371, filed on Jun. 15, 2012, which is a continuation of U.S. patent application Ser. No. 11/912,595, filed on May 21, 2008 (now U.S. Pat. No. 8,221,472), which is a U.S. National Stage of International Patent Application No. PCT/US2006/015692, filed on Apr. 25, 2006, which claims priority to U.S. Provisional Patent Application No. 60/674,877, filed on Apr. 25, 2005. These references are hereby incorporated by reference herein in their entireties.

TECHNICAL FIELD OF THE INVENTION

This invention relates to bone fixation devices and related methods of fixation. More specifically, this invention relates to bone anchors, such as screws and hooks for spinal fixation including polyaxial bone anchors, and related methods of spinal fixation.

BACKGROUND OF THE INVENTION

Many methods of treating spinal disorders are known in the art. One known method involves anchoring a screw or a hook to the vertebrae, and fixing the screws or hooks along a spinal rod to position or immobilize the vertebrae with respect to one another. The screws or hooks commonly have heads with U-shaped channels in which the spinal rod is inserted and subsequently clamped by a set screw or other fastener or locking cap. This method may commonly involve multiple screws or hooks, as well as multiple spinal rods. With this method, the spinal rod(s) may be shaped to maintain the vertebrae in such an orientation as to correct the spinal disorder at hand (e.g., to straighten a spine having abnormal curvature). Additionally or alternatively, the screws or hooks may be spaced along the rods(s) to compress or distract adjacent vertebrae.

Surgeons have often encountered considerable difficulty with this method because of trouble aligning the spinal rod(s) with the U-shaped channels in the heads of the screws or hooks. For example, the heads of the screws or hooks are often out of alignment with one another because of the curvature of the spine or the size and shape of each vertebrae. To facilitate easier insertion of the spinal rods into the U-shaped channels, and to provide additional flexibility in the positioning of the spinal rods and the screws and hooks, screws and hooks have been developed wherein the head (which includes the U-shaped channel) initially pivots with respect to the anchor member (e.g., screw shank or hook). One example of such a screw is disclosed in U.S. Pat. No. 5,586,984 to Errico et al., which is incorporated herein by reference.

The process of positioning and setting known bone anchors may be tedious and relatively time consuming, typically requiring more than one surgical tool to clamp the spinal rod and anchor member in desired positions. Even with a high degree of skill and care, the process of positioning a known set screw or other fastener on the bone anchor and then manipulating the screw or fastener to clamp or re-clamp the spinal rod and anchor member in place can take more time than desired during a surgical procedure or even resulting in the rod, anchor member, or both moving out of position before clamping is completed.

Therefore, a need still exists for bone anchors including polyaxial bone anchors that provide an improved mechanism for clamping the spinal rod and anchor member in their desired positions.

SUMMARY OF THE INVENTION

The invention is directed to a bone anchor including a polyaxial or monoaxial bone anchor for attaching a rod, such as a spinal rod or other device, to a bone, such as a vertebra. The bone anchor may include an anchor member (such as a screw, hook, or similar structure) for attachment to the bone and an anchor head of the bone anchor. The anchor head may be integral with the anchor member or may be a separate piece or component that couples with, and may polyaxially rotate about, the anchor member. The anchor head preferably has U-shaped openings for receiving the rod. The anchor head may have a recess for receiving the head of the anchor member such that the anchor member can initially polyaxially angulate or rotate with respect to the anchor head. The polyaxial bone anchor may also include a locking cap capable of clamping the rod and anchor member in desired positions.

The locking cap advantageously simplifies and preferably shortens the clamping process. The locking cap preferably includes a main body, a set screw, and a saddle. The set screw is preferably preloaded into the main body so that upon application of a torque, preferably below a predetermined amount, for example about 4.5 Newton-meters, the main body rotates with the set screw. Preferably, the saddle is in contact with or coupled to the set screw. Typically, after the anchor member is implanted into a bone and a rod is inserted into the bone anchor, the locking cap is positioned on top of the anchor head where features of the main body engage features of the head to allow the locking cap preferably to lock into place on the anchor head preferably with about a 90° turn or less. The instrument preferably engages the set screw and application of a rotary motion in a direction to lock the cap to the body (anchor head) also rotates the main body so that the main body is coupled to the bone anchor. Once the rod and anchor member are aligned as desired, the set screw can then be twisted into the anchor head, which causes the saddle to engage and then clamp the rod in place. As a result, the clamping of the rod may cause the anchor member in a polyaxial bone anchor to be clamped in place. Alternatively the anchor member may be locked to the anchor head in a polyaxial bone anchor independently of the rod to be clamped to the bone anchor. Advantageously, features of the main body and set screw allow the same tool to be used in a single action to position and lock the main body into the anchor head and to then rotate the set screw.

A bone anchor for attaching a fixation element to a bone according to one embodiment includes an anchor member (e.g., a bone screw) for attachment to said bone; a body having a top portion and a bottom portion, the body coupled to the anchor member proximate the bottom portion, the body forming a hollow interior and having a generally U-shaped channel in said top portion for receiving said fixation element; and a locking cap removably, non-threadably mountable to said top portion of said anchor head, the locking cap may have a main body (sometimes referred to as a locking ring) and a set screw threadably attached to the main body to engage and clamp the fixation element to the body. The main body of the locking cap may have one or more resiliently deflectable tabs and the body may have an inclined surface on its top surface, wherein the tab deflects over the inclined surface on the body upon rotation of the main body with respect to the body.

The main body and the set screw may be preloaded such that rotation of the set screw causes the main body to rotate. The set screw may be preloaded with the main body such that a force of about 2 to about 6 Newton-meters is necessary to allow the set screw to rotate with respect to the main body. The main body and set screw may be driven by a single instrument engaging only said set screw until said main body is locked in place on said housing. The body may further include a stop surface on its top surface to resist the main body from being removed from the body. The top surface of the body may further have a retention surface, and the stop surface and the retention surface may form a recess to retain the tab of the main body. The main body may rotate about 90° or less with respect to the body to secure the main body to the body. The main body of the locking cap may include one or more dovetail-shaped projections and the housing may include one or more dovetail-shaped grooves in the top portion. When the main body attaches to the body, the dovetail projections are received in the dovetail grooves to prevent splaying but the dovetail connection in some embodiments may not provide a force on the body during rotation of the main body. The locking cap further may include a saddle coupled to the set screw and independently rotatable with respect to the set screw return.

The bone anchor may optionally include a compressible collet having a bottom surface abutting a lower flange in the bottom portion of the body. The collet may have an extended shoulder that rests on the lower flange of the body. The bone anchor may further optionally include a sleeve having an internal recess that receives the collet and has a tapered inner surface to provide a compression force on the external tapered surface of the collet upon movement of the sleeve toward the bottom portion of the body to lock the anchor member. The sleeve preferably has a channel to receive the fixation element and the channel has at least a portion that has a smaller opening than the fixation element so that the fixation element is snap-fitted into the sleeve. The channel of the sleeve has an opening and the sleeve further has a top surface that has an inclined surface that interacts with a bottom surface of the locking cap to spread the sleeve opening. The body may have an assembly groove and the collet may have an extended shoulder where the assembly groove is configured to permit the bottom opening of the collet to expand to receive the head of the anchor member by receiving the extended shoulder.

A bone anchor for attaching a fixation element to a vertebrae according to another embodiment comprises an anchor member for attachment to said vertebrae; a body having a top portion and a bottom portion, the body forming a generally tubular-shaped element having an interior cavity, a top opening in the top portion communicating with the interior cavity and a bottom opening in the bottom portion communicating with the interior cavity, the top portion having an end wall, at least one groove and channel to receive the fixation element, the end wall has one or more dimples formed by an inclined surface and a straight wall, the inclined surface being inclined with respect to the end wall and the straight wall being substantially perpendicular with respect to the end wall; and a locking cap removably mountable to the top portion of the body, the locking cap comprising a locking ring and a set screw threadably attachable to the locking ring, the locking ring comprising one or more deflectable tabs and one or more projections; the deflectable tab is configured and adapted to interact with its respective dimple to deflect as the locking ring is rotated with respect to the body and the projection is configured and adapted to be received in its respective groove upon rotation of the locking ring. The end wall may further include an abutment surface, the abutment surface and the straight wall forming a recess for the deflecting tab upon rotation of the locking ring approximately 90°. The projection may be dovetail shaped and the groove may be dovetail shaped and wherein the respective dovetail shapes are adapted and configured so as not to provide engagement forces as the dovetail projection is received in the dovetail groove but the interaction of the projection and the groove may prevent the top portion from expanding beyond a predetermined distance.

The bone anchor may comprise a sleeve having a U-shaped channel adapted and configured to receive the fixation element, retention tabs, and a bottom portion having an internally tapered surface; and a compressible collet having an externally tapered surface, a hollow interior to receive a portion of the anchor member, a bottom opening, a plurality of flexible fingers and a shoulder extending beyond the external surface, the bottom opening of the collet configured and adapted in its natural state to be smaller than the portion of the anchor member received in the interior of the collet and having an expanded state that allows at least a portion of the anchor member to be moved therethrough; wherein the body comprises a flange proximate the bottom opening, an assembly groove in the bottom portion, and sleeve retention slots, the body containing the collet proximate the flange and the sleeve internally tapered surface contacting the collet external surface; whereby translating movement of the sleeve within the body compresses the resilient fingers of the collet inward to fix the anchor member relative to the head without the collet undergoing translating movement. The anchor member may be adapted and configured to be insertable into the body through the bottom opening and the collet may be adapted and configured to be insertable into the body through the top opening of the body but not the bottom opening, and wherein the anchor member may be insertable into the collet only when the shoulder of the collet is received in the assembly groove. The retention tabs of the sleeve may be positioned in slots formed in the body. The slots and retention tabs may be configured and adapted to align the fixation element channel of the sleeve with the fixation element channel of the body.

A method of manufacturing a bone anchor for a spinal fixation device that receives a fixation element may include the steps of providing an anchor member having a bone engagement portion and a head; providing a body having a top opening, a bottom opening, an interior cavity communicating with the top and bottom openings, a channel to receive the fixation element and an assembly groove, the bottom opening being smaller than the top opening; providing a collet having a bottom opening communicating with an interior cavity, and a shoulder proximate the bottom opening, the interior collet cavity being configured to receive at least a portion of the head of the anchor member and the bottom opening being smaller than at least a portion of the anchor member head; inserting the head of the anchor member through the bottom opening of the body; aligning the shoulder of the collet with the assembly groove of the body; inserting the head of the anchor member through the bottom opening of the collet while the collet is located in the interior cavity of the body and the shoulder is aligned with the assembly groove so that the collet expands and the shoulder is received into the assembly groove; forming a collet and anchor member assembly by allowing the collet to retract so that the shoulder is moved out of the assembly groove and the head of the anchor member is retained by the collet; repositioning the collet and anchor member assembly so that the shoulder is not aligned with the assembly groove. The method of assembly may further comprise providing a sleeve having an internally tapered surface, retention tabs and a channel to receive the fixation element; inserting the sleeve into the interior cavity of the body through the top opening; and positioning the sleeve so that at least a portion of the internally tapered surface overlies at least a portion of the exterior surface of the collet and so that the retention tabs snap into slots formed in the body after the collet anchor member assembly is formed in the body.

A method of fixing the vertebrae of the spine using a first bone anchor having a first anchor member and a first anchor head having a first rod-receiving opening or channel, and a second polyaxial bone anchor having a second anchor member and a second anchor head having a second rod-receiving opening or channel is also described. The method may include inserting the first anchor member into a first vertebra and inserting the second anchor member into a second vertebra. The first anchor member may be inserted into a lateral mass of a first vertebra, and the second anchor member may be inserted into a lateral mass of a second vertebra. As an example, at least one of the first and second vertebrae preferably may be selected from the group of vertebrae comprising the lumbar or thoracic regions of the spine although other areas of the spine are contemplated.

After the bone anchor is inserted in the bone, a rod may be inserted into the rod receiving channel from the top of the bone anchor. The locking cap may then be placed on the top of the bone anchor and rotated 90° or less to engage the locking cap with the bone anchor, and in particular a main body of the locking cap engaging the anchor head of the bone anchor. With the locking cap in this position, the rod is positioned in the rod receiving channel of the bone anchor and may undergo translating and/or rotating movement in the rod receiving channel. Using the same tool that was used to twist the main body to engage the main body to the anchor head, the set screw may then be rotated upon application of a predetermined torque to the set screw so that the set screw can rotate independently of the main body. Further rotation of the set screw clamps the rod in position, and may further clamp the position of the anchor head or body to the anchor member, which may be, for example, a screw or hook. Alternatively, with the locking cap engaged to and covering the opening of the anchor body, the position of the anchor head to the anchor member may be clamped and fixed, although the spinal rod may undergo rotational or translating movement in the rod receiving channel.

The method may also include coupling the rod to a bone anchor by locking the main body to the anchor head, positioning the rod relative to one or both of the bone anchors, for example, by rotating or translating the rod in one or more of the rod receiving channels and clamping the rod in one or more of the bone anchors, for example, by rotating the set screw of a respective bone anchor.

The method may further include loosening the set screw so that the rod can be moved relative to the bone anchor by, for example, rotating the set screw in an opposite or second direction, repositioning the rod in one or more of the rod receiving channels, and/or repositioning the anchor head relative to the anchor member of one or more of the bone anchors, and relocking/clamping the rod into position and/or relocking/clamping the anchor member relative to the anchor head.

The method may still further include rotating the locking cap in an opposite or second direction in order to loosen or remove the locking cap from the bone anchor, and more particularly rotating the main body in an opposite or second direction to disengage and, if desired, remove the locking cap from the bone anchor. The main body may be rotated by using the same first tool used to couple the main body to the anchor head and to tighten the set screw, or alternatively a second tool may be used to loosen the main body, or alternatively both the first and second tools may be used to loosen the main body from the anchor head.

BRIEF DESCRIPTION OF THE DRAWINGS

The detailed description will be better understood in conjunction with the accompanying drawings, in which like reference characters represent like elements, as follows:

FIG. 7B1-5 are front, side, top, sectional, and partial cross-sectional views, respectively, of an embodiment of a sleeve showing representative dimensions.

FIG. 8 is a perspective view of an embodiment of a slotted collet according to the invention;

FIG. 9 is a perspective view of the main body of a locking cap according to the invention;

FIG. 10 is a perspective view of the set screw of a locking cap according to the invention;

FIG. 11 is a perspective view of the saddle of a locking cap according to the invention;

FIGS. 12-15 are top, front cross-sectional (taken along line A-A of FIG. 12), side cross-sectional (taken along line B-B of FIG. 12), and enlarged partial cross-sectional views, respectively, of the saddle of FIG. 11 showing representative dimensions;

FIGS. 16-21 are perspective, top, front, front cross-sectional (taken along line A-A of FIG. 17), side, and side cross-sectional (taken along line B-B of FIG. 17) views, respectively, of the assembled locking cap comprising the components of FIGS. 9-11;

FIGS. 22-26 are perspective, top, front cross-sectional (taken along line A-A of FIG. 23), and two enlarged partial cross-sectional views, respectively, of the polyaxial bone anchor with the locking cap inserted and in an open, nonengaged or uncoupled position and with the rod unlocked;

FIG. 27 is a top view of the locking cap inserted and in an open position on the anchor head;

FIGS. 28-32 are perspective, top, front cross-sectional (taken along line A-A of FIG. 29), and two enlarged partial cross-sectional views, respectively, of the polyaxial bone anchor with the locking cap inserted and in a closed, engaged or coupled position and with the rod unlocked;

FIGS. 34-38 are perspective, top, front cross-sectional (taken along line A-A of FIG. 35), and two enlarged partial cross-sectional views, respectively, of the polyaxial bone anchor with the locking cap inserted and in a closed, engaged or coupled position and with the rod locked; and FIGS. 39 and 40 are perspective views of illustrative embodiments of a monoaxial bone anchor and a spinal hook employing a locking cap.

DETAILED DESCRIPTION OF THE INVENTION

Figure 1:
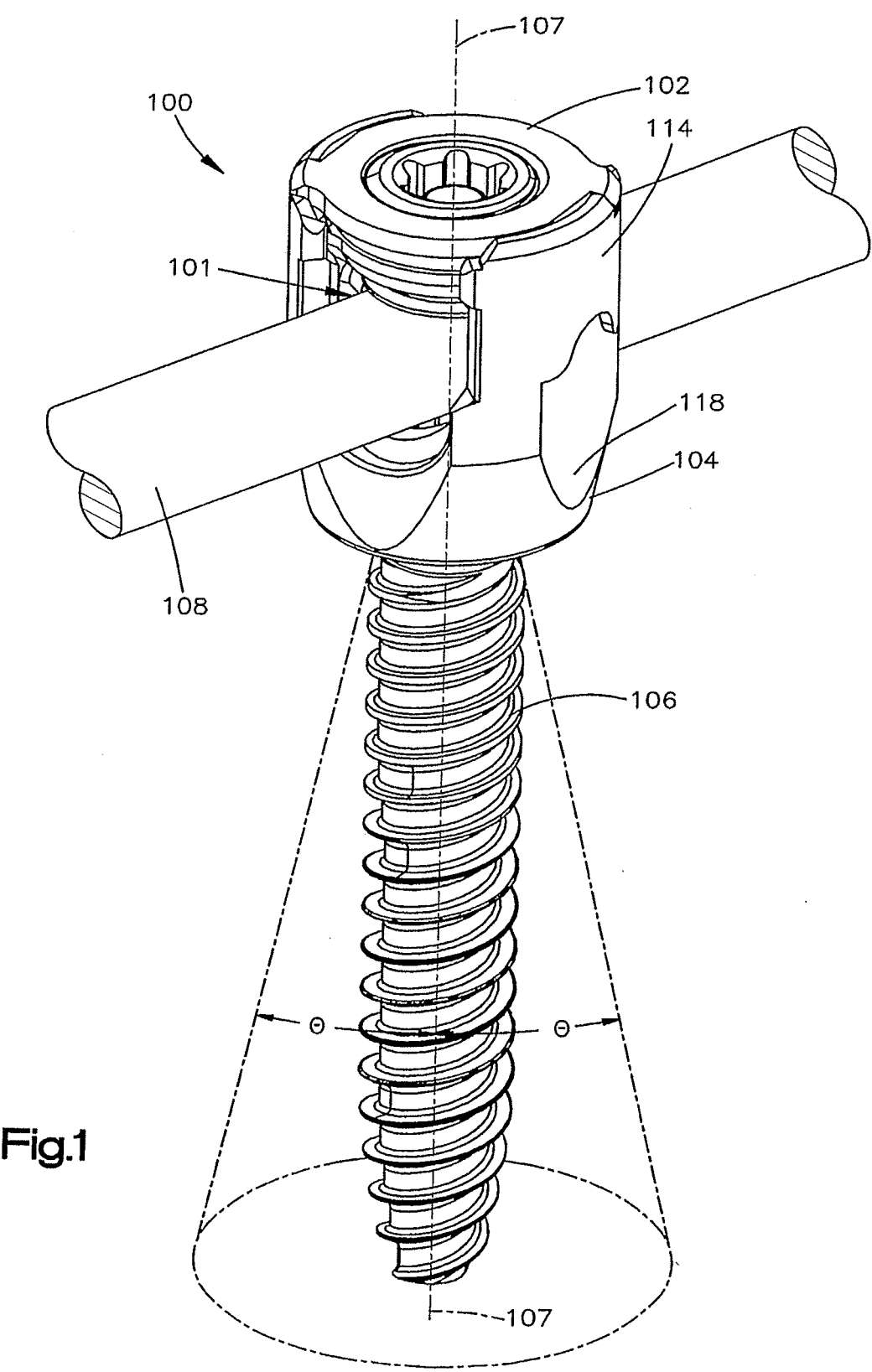
FIGS. 1-6 are perspective, front, side, front cross-sectional (taken along line A-A of FIG. 6), side cross-sectional (taken along line B-B of FIG. 6), and top views, respectively, of an illustrative embodiment of a polyaxial bone anchor according to the invention.
Figure 5:
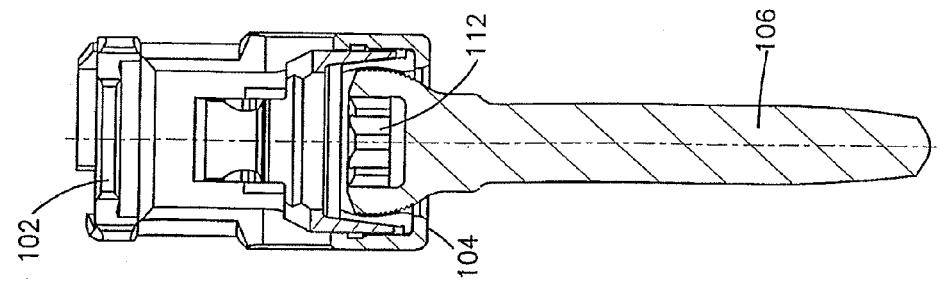
Figure 4:
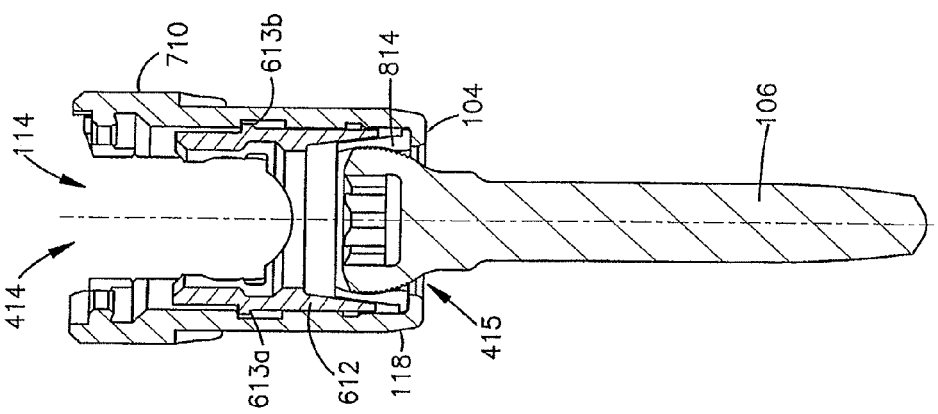

While the bone anchor will be illustrated and described herein with reference to certain preferred or exemplary embodiments, the invention should not be limited to these preferred or exemplary embodiments. Furthermore, the features described and illustrated herein can be used singularly or in combination with other features and embodiments.

FIGS. 1-6 show an embodiment of a polyaxial bone anchor. Polyaxial bone anchor 100 includes a locking cap 102 (not shown in FIGS. 2-5), an anchor head 104, and an anchor member 106. Bone anchor 100 may also be a monoaxial bone anchor such that the anchor member and anchor head are integral members that are fixed together (See FIG. 39). Anchor head 104 (sometimes referred to in the art as the body) has a generally U-shaped opening 101 for receiving a spinal rod 108 (note that spinal rod 108 is not shown in FIGS. 2-6) or other device, such as, for example, a plate. Anchor member 106, which may be a bone screw, hook, or other similar structure, is coupled to anchor head 104 such that it can preferably polyaxially rotate with respect to head 104. In one embodiment of the invention, anchor member 106 can angularly rotate about axis 107 by an angle θ of preferably at least about 25° in any direction (i.e., the angular rotation of anchor member 106 forms a cone of about 50°), although other ranges of angulation are contemplated. One or more polyaxial bone anchors 100 may be attached, for example, to the vertebrae via respective anchor members 106, and a spinal rod 108 or other device can be inserted into the U-shaped openings 101 and thereafter locked to correctly align the spine or treat other spinal disorders.

Figure 7A:
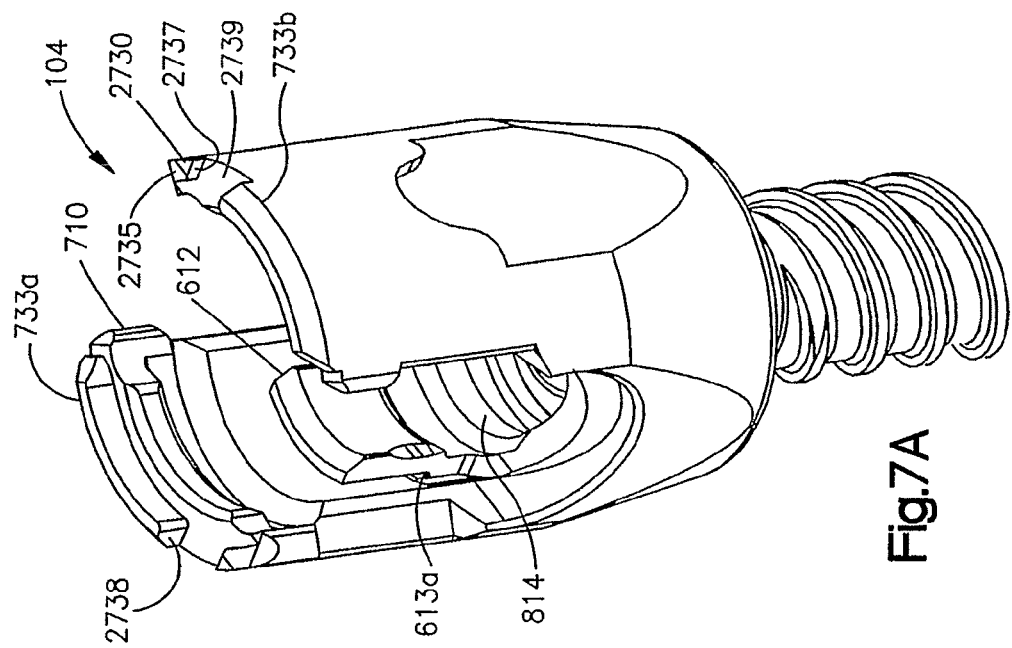
FIG. 7A is a perspective view of the anchor head without the locking cap.
Figure 6:
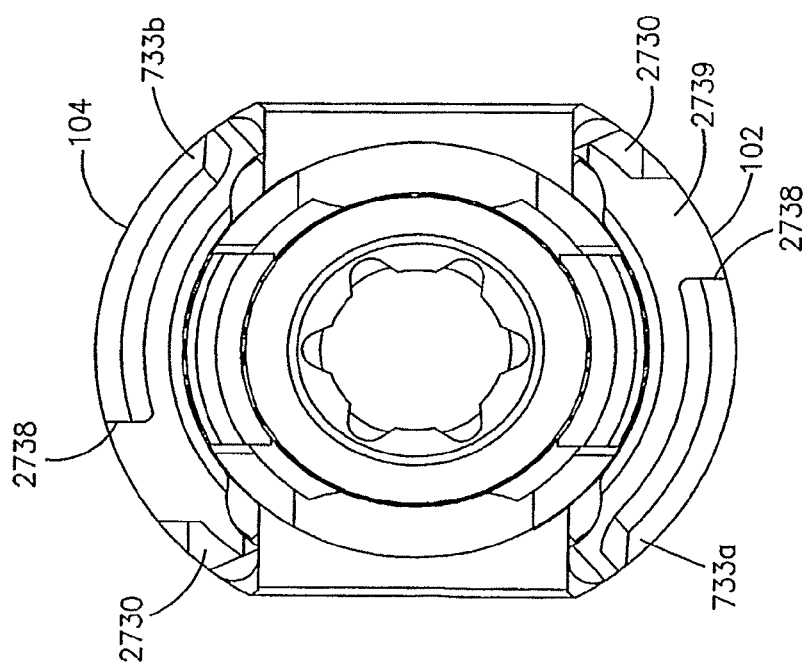
Figure 7:
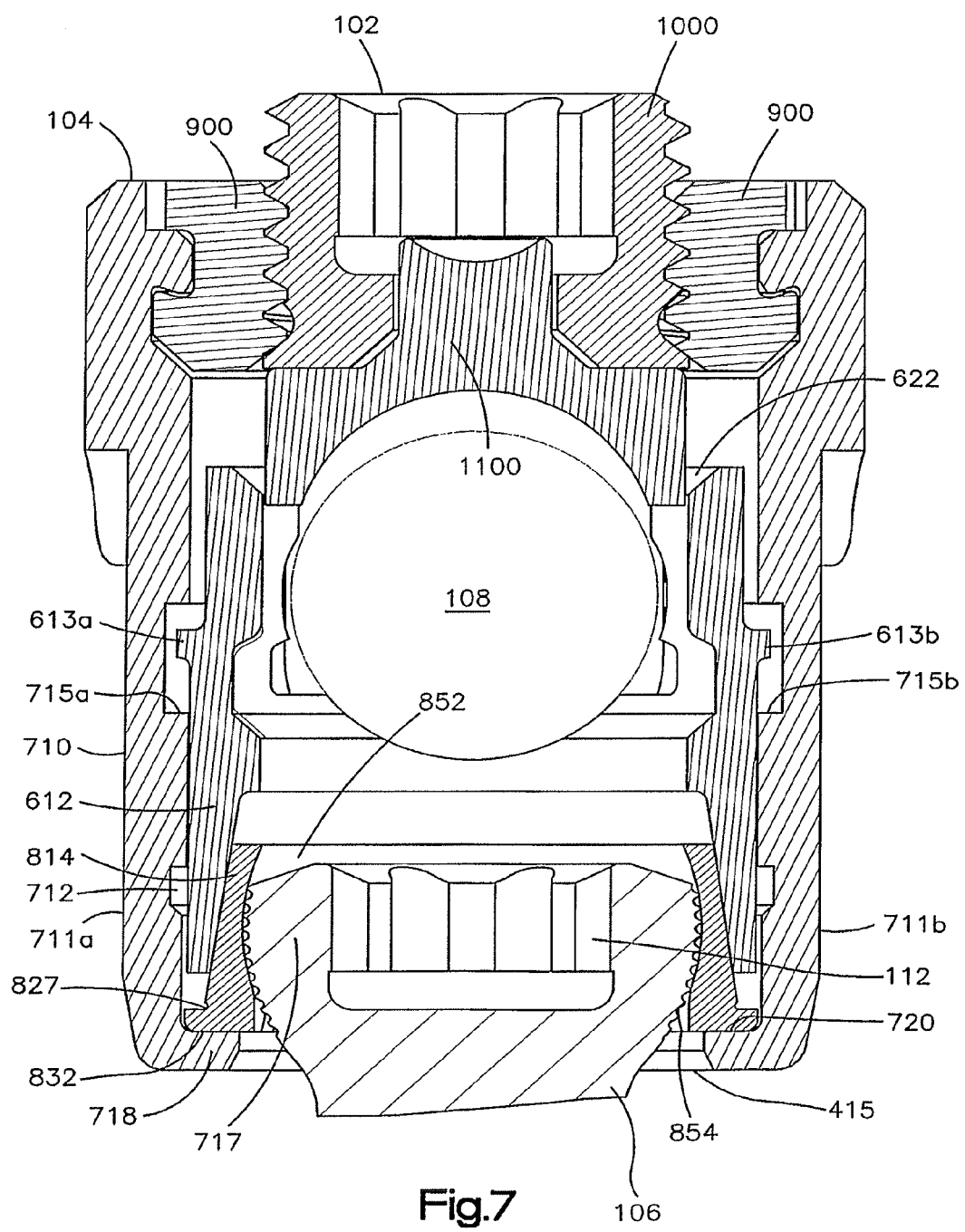
FIG. 7 is front cross-sectional view (taken along line A-A of FIG. 6) of the anchor head and locking cap of the polyaxial bone anchor of FIGS. 1-6.
Figure 33:
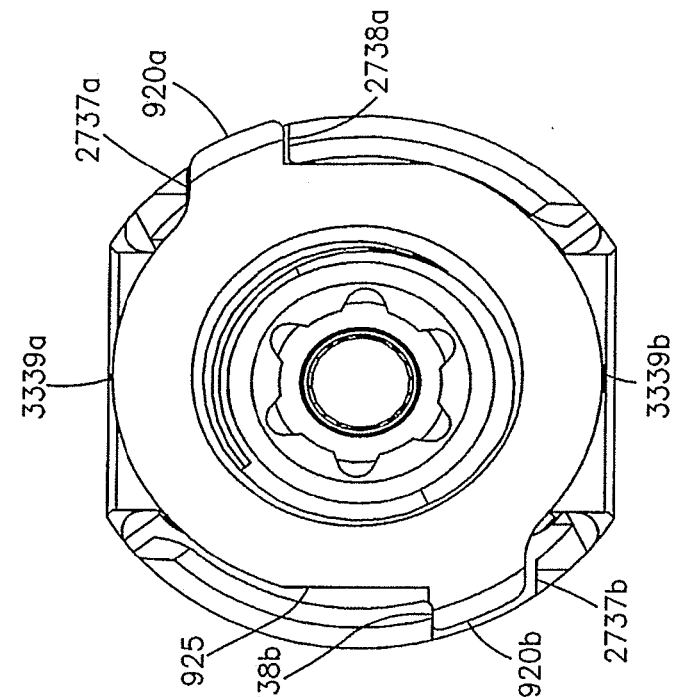
FIG. 33 is a top view of the locking cap inserted and in a closed position on the anchor head.

As shown in FIGS. 7 and 7A, anchor head 104 includes a generally cylindrical, hollow housing 710, and may optionally contain a generally U-shaped sleeve 612, and a collet 814. Housing 710 has generally cylindrical, untapered interior wall portions 711a,b, but alternatively can have at least some wall portions that are tapered inward toward anchor member 106. The exterior shape of housing 104 may be generally cylindrical and may have tapered or straight wall portions. Other exterior shapes for housing 104 are also possible. Sleeve 612 has retention tabs 613a,b that snap into respective slots 715a,b in opposite walls of housing 710 as sleeve 612 is inserted preferably downward through housing 710. In one embodiment of the invention, slots 715a,b are sized to allow sleeve 612 to move up and down about 1.5 mm, although other distances are contemplated. One or more slots may be formed in housing 710 depending upon the number of retention tabs. There may be more slots formed than retention tabs. Moreover, the slots can extend or be formed across the width or circumference of the interior housing wall so that the sleeve can rotate (spin) in the housing or the slots can be formed to be approximately the same width as the tabs so that the sleeve cannot rotate (spin) in the body. The configuration and interaction of the retention tabs on the sleeve and slots can be designed so that the sleeve will be aligned in the body, or so that no alignment feature is provided. Accordingly, the retention tabs can interact with the slots to align the fixation element channel of the sleeve with the fixation element channel of the body. The retention tabs and slots may be reversed so that the tabs may be formed on the housing and the slots may be formed on the sleeve. Anchor head 104 has a top portion 114 and a bottom portion 118 and a bore 116 extending along longitudinal axis 107. A top opening 414, bottom opening 415 and U-shaped opening 101 communicate with bore 116. Preferably a flange 718 extends inward proximate bottom opening 415. Flange 718 preferably forms a substantially flat interior surface 720 that is preferably substantially perpendicular to longitudinal axis 107. Surface 720 may also be curved, and may be inclined at non-perpendicular angles with respect to axis 107.

Anchor member 106 preferably has a curved head 717 which is shaped and dimensioned to fit within housing 710 and an internal space 815 of collet 714 (note that the top portion of curved head 717 is cut away in FIG. 7 to show collet 714). Curved head 717 may be substantially spherical or frustospherical and preferably has a recess 112 that is keyed to receive a hex wrench, torque wrench, or other known driver to allow anchor member 106 to be implanted by rotating into, for example, a vertebra.

FIG. 7B1-5 show various views of a sleeve 612. Sleeve 612 preferably has a U-shaped channel 610 to receive spinal rod 108 or some other fixation element. Channel 610 is formed by stanchions 615a and 615b. Sleeve 612 is generally cylindrically shaped, although other shapes are possible, and has a longitudinal bore 616. The stanchions 615a,b formed on the top part of the sleeve are flexible and preferably include the retention tabs 613a,b. Instead of two retention tabs, one or more retention tabs may be utilized. A top opening 618 communicates with the bore 616 and the channel 610. The stanchions 615a,b form partial cylindrical or curved walls. The width of U-shaped openings 610 at the top opening 618, formed by the outer edges of the curved wall of the stanchions 615a,b, preferably are smaller than the diameter or width of the spinal rod 108 so that the rod flexes the stanchions upon insertion into the sleeve and snaps into place in the sleeve. The top inner surface 622 has a taper or incline at the top opening 618. The smaller opening 610 formed by the flexible stanchions permits the stanchions 615a,b to flex, compress and grip the rod when it is inserted into the U-shaped channel 610 of the sleeve 612. The tapered top inner surface 622 may facilitate the spreading of the stanchions 615a,b.

A recess 625 is formed in the lower or bottom portion 626 of the sleeve 612. The exterior surface 628 of the bottom portion may be straight and generally cylindrically shaped. The recess 625 communicates with bottom opening 630 and preferably with bore 616. The interior walls forming recess 625 preferably are at least partially tapered as show in FIG. 7 B1. The angle of the taper is preferably about 8° although other angles are contemplated. The recess 625 as described below receives the collet 814.

The diameter of the sleeve 612 is preferably about 9 mm to about 10 mm although other diameters are contemplated. The width or length of the openings 610 formed by the stanchions 615a,b at its smallest width is preferably about 5.9 mm (for a 6.0 mm spinal rod), although other dimensions are contemplated. The height of the sleeve 612 is preferably approximately about 9 mm to about 10 mm although other dimensions are contemplated. Alternatively, sleeve 612B may be of other dimensions.

FIG. 8 shows an embodiment of a collet 814. The collet preferably has slots 806 to create resilient fingers 810 that can deflect outward to allow head 717 of the anchor member to be inserted within the internal space 815 formed by the collet. The internal space 815 is formed by a bore 850 that communicates with top opening 852 and bottom opening 854. Slots 806 may also have a radius or circular shaped portion 808 as a stress relief and to provide better resiliency to fingers 810. Although the slots are shown as extending from the lower or bottom end 812 into which head 717 of the anchor member is inserted, the slots can alternatively extend from the top end 820, or alternatively slots 806 can extend from both bottom end 812 and top end 820. In one embodiment, collet 814 may have a slot that extends from the top end 810 through to bottom end 812 so that it may form a C-ring. The arrangement, shapes, and dimensions of the slots may be alternatively different than shown. The bottom opening 854 preferably is sized so that it is smaller than the maximum diameter of the head 717 of the anchor member. The internal space 815 preferably has a larger diameter than the bottom opening 854 to accommodate.

Collet 814 preferably has an externally tapered surface 822. The exterior tapered surface 822 preferably is about 8° and preferably substantially matches the taper of the interior surface of the recess area 625 of the sleeve 612 to form what is sometimes referred to as a Morse Taper. The collet also has an interior surface 824 preferably shaped to substantially match the shape of head 717. Preferably the interior surface 824 is semi-spherically shaped to match the shape of head 717, although surface 824 may also be conically shaped or have other shapes. Collet 814 is made of a resilient material, preferably titanium alloy, that can be compressed around head 717 to retain anchor member 106 securely in place. Preferably the material of the collet is softer than the material of sleeve 612 and anchor member 106. In one embodiment of collet 814, top inside diameter 816 is about 6.3 mm and height 818 is about 3.7 mm. Alternatively, collet 814 may be of other dimensions.

In a preferred embodiment, collet 814 may have a ring 826 forming an extended shoulder 828 around the bottom end 812. Preferably an undercut radius 827 is formed at the exterior surface where the tapered exterior surface 822 meets the extended shoulder 828. The interior surface 830 (FIG. 25) opposite the extended shoulder 828 preferably is flat and substantially perpendicular to the substantially flat bottom surface 832, although surface 830 may be curved and non-perpendicular to bottom surface 832. The bottom ring 826 preferably provides increased surface area at bottom surface 832 to rest on the flange 718 formed proximate the bottom opening 415 of the housing 710. The extended shoulder 828 may provide extra rigidity to the collet 814 and may better retain the bone anchor in the housing 710.

Collet 814 is preferably inserted into top end 114, or the U-shaped rod receiving channel 101, and is sized so that it can be inserted into bore 116 of the anchor head from top 114, but is also sized and dimensioned so that it is retained in the lower end of bore 116 of the anchor head. In other words, the diameter of the collet is such that it can pass through the top opening 414 of bore 116, but preferably cannot pass through the bottom opening 415 of bore 116. Alternatively, fingers 810 of the collet can be compressed to allow the collet to be inserted through bottom opening 415, and once within anchor head 104, the fingers can expand. Thus, the collet can be inserted into the top or bottom opening of the anchor head. After the collet is inserted, sleeve 612 may be inserted into the top opening or from the side through the U-shaped rod receiving channel 101 so that the lower end 626 of the sleeve is positioned around top end 820 of the collet. Sleeve 612 may be pressed down until retention tabs 613a,b snap in retention slots 715a,b. Anchor member 106 may be inserted from bottom opening 415 of bore 116. Collet 814 may then be inserted down bore 116 and snapped over head 717 of anchor member 106. Alternatively, collet 814, or collet 814 and sleeve 712 may be inserted and positioned in anchor head 104 and head 717 of anchor member 106 inserted into bottom opening 414 and snapped into the collet. When head 717 is inserted into the bottom opening 812 of the collet 814, the sleeve is positioned to allow the collet to expand so that the head may pass through bottom opening 812 and thereafter the collet would contract to hold the head 717 of the anchor member 106.

If the collet 814 with the extended shoulder 828 is used, the body or housing 710 preferably has an assembly groove 712 preferably formed in the bottom portion 118 of the housing 710. Preferably the assembly groove is formed in the interior walls of the housing 710 between the flange 718 and the sleeve retention slots 715a,b, although other locations for the assembly groove are contemplated. The assembly groove 712 permits the bottom opening 854 of the collet 814 to expand while it is inside the bore 116 of the housing 710 to permit the head of the anchor member to pass through the smaller opening 854 of the collet 814.

In a preferred assembly method, the collet 814 is inserted into the top opening 414 of the housing 710. The head 717 of the anchor member 106 is inserted through the bottom opening 415 of the housing. With the extended shoulder 828 of the collet aligned with the assembly groove 712 in the housing 710, the head 717 of the anchor member is inserted through the bottom opening 854 of the collet. Since the bottom opening 854 is smaller than the head 717 of the bone anchor 106, the collet expands and the extended shoulder 828 is temporarily received in the assembly groove 712 until the maximum diameter of the head 717 passes through the opening 854. As the head 717 is inserted further into the internal space 815, the fingers 810 retract and the extended shoulder 828 moves out of the assembly groove. Thereafter the anchor member 106 and collet 814 assembly are moved so that the extended shoulder 828 is no longer aligned with the assembly groove 712 and the anchor member is retained by the collet such that the anchor member can angulate and rotate within the collet but cannot be released from the collet because the collet cannot expand sufficiently to permit the head 717 to pass through the bottom opening 854. Preferably the collet and anchor member assembly are moved so that the bottom surface 832 of the collet contacts and is retained by the flange 718 of the housing 710.

With the collet and bone member assembly in the housing 710, the sleeve 612 may be inserted into the top opening 424 of the housing and moved down so that the recess 625 receives and overlaps with a portion of the collet 814. The sleeve is inserted in the housing 710 preferably so that the retaining tabs 613a,b are received in the retaining slots 715a,b. In this manner, the sleeve is retained in the housing 710 and in turn retains the collet 814 and the anchor member 106 in the housing. More preferably, the sleeve is moved down into housing 710 so that its internal tapered surface 622 overlaps with the external tapered surface 822 of the collet 814 when the retention tabs 613,ab are received in the retaining slots 710a,b. With the sleeve inserted, the anchor member preferably is still permitted to polyaxially angulate and rotate about longitudinal axis 107 of housing 710.

FIG. 7 further shows locking cap 102 locked into anchor head 104. Locking cap 102 preferably includes a main body or locking ring 900 (also shown in FIG. 9), a set screw 1000 (also shown in FIG. 10), and a saddle 1100 (also shown in FIG. 11). In one embodiment, main body 900 preferably has an outside diameter 919, measured from tab 920a to tab 920b, of about 12.5 mm, and set screw 1000 preferably has a height 1018 of about 4.5 mm and preferably an outside diameter 1019 of about 7.0 mm. Alternatively, main body 900 and set screw 1000 may be of other dimensions. FIGS.

13-14 show various views of saddle 1100. Alternatively, saddle 1100 may be of other dimensions.

FIGS. 16-21 show various views of locking cap 102. Set screw 1000 has external threads 1023 that mate with internal threads 921 of main body 900. Advantageously, set screw 1000 cannot be screwed out of main body 900 in the direction of up arrow 1824 in FIG. 18 because of flared portion 1925 at the bottom of set screw 1000. Set screw 1000 is preferably preloaded into main body 900 before locking cap 102 is used in a bone anchor. More specifically, set screw 11000 is rotated in the direction of arrow 1824 (in FIG. 18) so that portion 1925 engages bottom end 1926 of the internal threads of main body 900 and tightened so that a friction fit is created. The friction fit is such that it takes a certain predetermined torque ST applied to the set screw to free the set screw from main body 900. Until the predetermined torque ST is applied, any rotational torque applied to the set screw rotates the set screw and the main body. The torque to free the set screw preferably may be about 2 to about 6 Newton-meters, and more preferably about 4.5 Newton-meters. In one embodiment, set screw 1000 has a star socket 1727. Alternatively, set screw 1000 can have other types of sockets or recesses keyed to other known drivers or tools. Advantageously, as described in more detail below, a single tool or drive mechanism can drive in a single action both main body 900 and set screw 1000 simultaneously to lock locking cap 102 in place on an anchor head and then continue driving set screw 1000 alone until a rod inserted in the bone anchor and an anchor member are clamped in place.

Saddle 1100 is preferably coupled to set screw 1000. That is, set screw 1000 is fitted onto upper portion 1122 (see FIG. 11) of saddle 1100, the upper portion 1122 preferably being cylindrically shaped, and then the top of portion 1122 is splayed slightly to create a flange. More particularly, upper portion 1122 forms a stem 1130 which is fitted through a bore 1020 that communicates with recess 1727 in the set screw 1000. After the top portion 1132 of stem 1130 protrudes into the recess 1727, the top portion where a wall has been formed by depression 1136 is flared outward to couple the saddle 1100 to the set screw 1000. The saddle is coupled to set screw 1000, but is free to rotate with respect to et screw 1000 about an axis 1310 (see, e.g., FIG. 19). Stem 1130 has a tapered transition region 1135 where it joins lower portion 2129. The bottom opening of bore 1020 has a tapered recess region to accommodate transition region 1135. Saddle 1100 has a recess 1320 which has a radius of curvature about the same as the spinal rod.

Saddle 1100 preferably has helical grooves 2130 on lower portion 2129 (see FIG. 21) to enhance gripping of the rod. Preferably the helical grooves are inclined, similar to screw threading, and thus not perpendicular to the axis formed by the recess 1320. The grooves generally run in the direction of arrow 2135 (shown in FIG. 13A) from extending portion 1142 to extending portion 1144. The helical grooves preferably are only slightly inclined and may provide increased clamping strength on the rod as they are slightly offset from being perpendicular to the longitudinal axis of the rod.

Housing 710 has an end wall or top surface 730 that preferably has one or more of the following features to assist in cooperating with the locking cap 102 to attach the locking cap to the bone member. The top surface 730 (also referred to as the end wall) preferably may have dimples 2730a,b formed by respective ramped surfaces 2735a,b and straight-walled stop surfaces 2737a,b. Top surface 730 may also contain retention surfaces 2738a,b as well as structures 733a,b. The outer edge 735 of the top surface 730 may be beveled or inclined. The main body 900 may have extending tabs 920a,b and straight surface 925a,b. The extending tabs 920a,b form abutment surfaces 930a,b. Preferably the abutment surfaces 930a,b are substantially perpendicular to the straight surfaces 925a,b, although they may be non-perpendicular. The outer edge of the tabs 920 may also have a beveled or inclined surface. Main body 900 also preferably has flanges 3236 and 3238 and extending surface 2632. Flanges 3236 and 3238 will interact with grooves 2636 and 2638 respectively formed in housing 710. The interaction of these structures of the housing with the main body 90 will be described in more detail below.

To lock (i.e., clamp) a rod and anchor member in place in a bone anchor, locking cap 102 is positioned on top of housing 710 as shown in FIGS. 22-27. Locking cap 102 and particularly tabs 920a,b are oriented with respect to dimples 2730a,b on the top surface 730 of housing 710 as shown in FIG. 27. Preferably surface 2632 of main body 900 (best seen in FIG. 26) extends slightly beyond surface 2634 of housing 710 when main body 900 is oriented in housing 710 as shown in FIGS. 22-27. As such locking cap 102 is pressed downward until it snaps into the position shown in FIGS. 22-27. Note that ramp surface 2642 on housing 710 and ramp surface 2644 on main housing 900 facilitate this snap-in action. That is, the ramp surfaces will interact to flex (e.g., elastically deform) the upper portion of the housing so the main body can snap into position. At this stage, locking cap 102 is inserted into the anchor head and is in an open, unengaged or uncoupled position. Rod 108 is unlocked (i.e., unclamped); note space 1108 between rod 108 and saddle 1100 in FIG. 24. Furthermore, anchor member 106 is also unlocked (i.e., unclamped); note space 2508 between sleeve 612 and housing 710 in FIG. 25. At this stage, collet 814 is not compressed against the head of anchor member 106, thus allowing member 106 to axially rotate or angulate, as discussed above. Preferably the saddle is inserted into the top opening 618 of the sleeve when the locking cap 102 is inserted into the housing 710. More preferably, the dimensions of the saddle that fit within the opening 618 of the sleeve are larger than the opening 618 in its natural state such that the saddle flexes the stanchions 615a,b outward. The tapered top inner surface 622 of the sleeve may facilitate the spreading of the stanchions 615a,b.

Locking cap 102 is next preferably rotated about 90° (i.e., about ¼ turn) in the direction of arrow 2731 (see FIG. 27). Note that the locking cap cannot be rotated in the opposite direction because structures 733a,b on housing 710 (see FIGS. 7A and 27) would contact tabs 920a,b on main body 900. As locking cap 102 is rotated in the direction of arrow 2731, flexible resilient tabs 920a,b encounter dimples 2730a,b on housing 710 (see FIG. 27). Dimples 2730a,b preferably have respective beveled or ramp surfaces 2735a,b to facilitate moving tabs 920a,b up and over respective dimples 2730a,b in order to attach the locking cap in the closed position to anchor head 104. The main body 900 does not have screw threads that may be cross-threaded when attaching locking cap 102 to anchor head 104. Ramp surfaces 2737a,b of dimples 2735a,b are configured such that a predetermined torque RT is needed to slide and deflect tabs 920a,b over the ramp surfaces. The predetermined torque RT to overcome and slide over the dimples is preferably less than the predetermined set screw torque ST (RT<ST) such that the torque applied to the set screw may rotate both the set screw and main body together (i.e., the locking cap) into the closed position. In this exemplary embodiment, a single instrument or tool applied to the set screw can rotate the main body from the open to the closed positions. The main body is rotated in the direction of arrow 2731 in FIG. 27 until the tabs pass straight-walled surfaces 2737*a,b* so that the tabs return to their unflexed position and rest in the recesses 2739*a,b* formed between stop surfaces 2737*a,b* and retention surfaces 2738*a,b*. Preferably the height of the tabs 920 is approximately the height of the dimples (e.g., straight wall stop surface 2737) and the height of retention surface 2738 so that when tabs 920 are in recesses 2739, the top surface of the tab is approximately level with the top surface of structures 733. Surfaces 2737*a,b* are preferably straight-walled such that if the locking cap is rotated in the opposite direction after sliding over the ramp surfaces, the respective tabs 920*a,b* would abut against straight walled surfaces 2737*a,b* in the closed position. Surfaces 2737*a,b* thus act as stops to prevent locking cap 102 from rotating backward (to the open position) unless sufficient force is applied. If the user continues to rotate the cap in the direction of arrow 2731 (FIG. 27), the tabs 920*a,b* will contact abutment surfaces 2738*a,b* and resist, and more preferably, prevent further rotation of main body 900.

Figure 32:
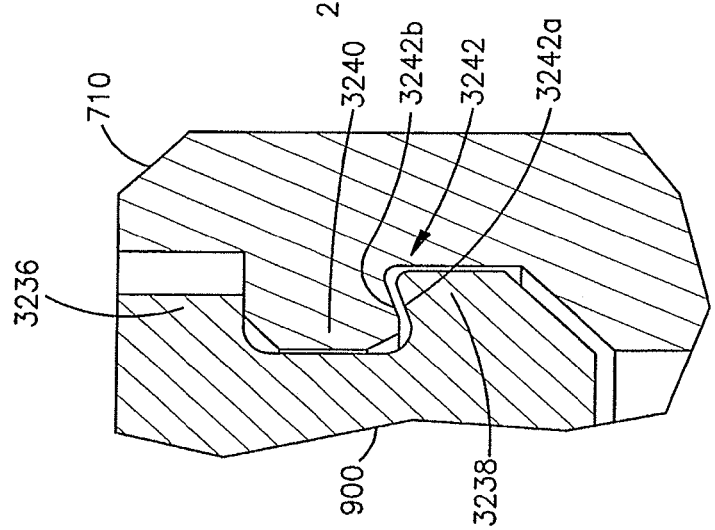
Figure 31:
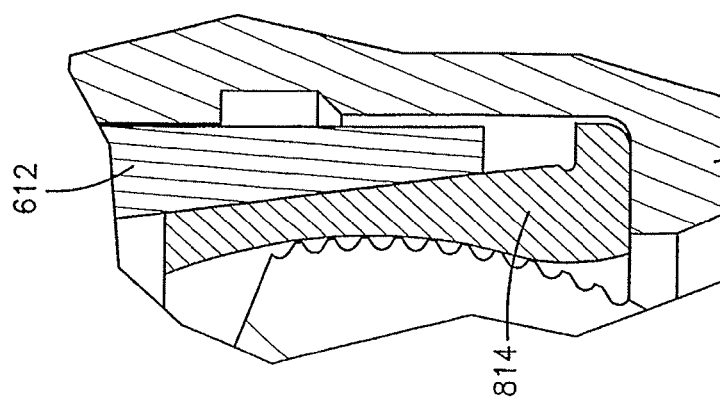

FIGS. 28-33 show locking cap 102 inserted into the anchor head and in the closed or engaged or coupled position. As shown in FIG. 32, flanges 3236 and 3238 on main body 900 are positioned in corresponding grooves 2636 and 2638, respectively, on housing 710, and flange 3240 on housing 710 is positioned in a corresponding groove 3241 on main body 900. Flange 3238 preferably has an inclined surface 3242 that tapers from a diameter approximately equal to the inside diameter of anchor head 104 to the maximum diameter illustrated in FIG. 32. Flange 3238 may also have inclined surfaces 3222 and 3224 formed on their sides so that the flange 3238 increases in thickness. Flange 3236 preferably is similarly configured to flange 3238. The inclined surfaces 3242, 3222 and 3224 may facilitate flange 3238 to enter the corresponding groove 2638. Preferably, flange 3238 and groove 2638 are dovetailed, as shown at area 3242, to prevent any anchor head splaying that may occur. More specifically, the projection or flange 3238 has an angled surface 3242*a* as shown in FIG. 32 that corresponds to angled surface 3242*b* such that if an outward force is applied to the anchor head 104, as a result, for example, of clamping forces as the rod is clamped into position, surface 3242*a* of flange 3238 would contact surface 3242*b* of flange 3240 and prevent anchor head 104 from expanding or splaying. Groove 2636 preferably is similarly configured to groove 2638. At this stage, rod 108 is still unlocked; again, note the space between rod 108 and saddle 1100 in FIG. 30. Accordingly, as a comparison, FIGS. 31 and 25 show the about 90° turn to set locking cap 102 in the closed position did not change substantially, if at all, the relative positions of sleeve 612 and collet 814. In this closed position, the tabs 920 interacting with the stop surfaces 2737 prevent the locking cap from rotating to the open position while the interaction of the flanges 3236, 3238 with grooves 3236, 3238 prevent the locking cap from being lifted out of housing 710.

Advantageously, the same tool or driving mechanism used to insert and close locking cap 102 in anchor head 104 can be used in a continuous action to further rotate set screw 1000. The main body and set screw rotate together until the main body snaps into the closed position, at which time tabs 920*a,b* contact structures 2738*a,b* on top end 114 of anchor head 104 of bone anchor 100. As tabs 920*a,b* contact structures 2738*a,b* on anchor head 104, the torque to rotate the main body and set screw increases until the torque applied is larger than the predetermined set screw torque ST, at which point the friction connection holding the set screw to the main body is overcome and the set screw continues to rotate alone independent of the main body. The same tool can be advantageously used to move the set screw downward in anchor head 104 to the locked position as described below. In addition, the same instrument used to free the set screw from the main body, and which may also be used to move the set screw downward to the rod locked position where the rod is clamped, may also be used to loosen the set screw (i.e., rotate the set screw in the opposite direction) until the flared thread portion 1925 of the set screw engages the main body, at which time, both the main body and set screw may rotate together. If sufficient force is applied in the direction opposite arrow 2731, the locking cap can be returned to the open position. Note that the torque required to overcome the blockage of flared thread portion 1925 by the main body is preferably greater than the torque TT required for tabs 920*a,b* to deflect over the straight wall surfaces 2737*a,b*.

Optionally, main body 900 may have a pair of oppositely positioned scalloped cutouts where straight sections 925 of main body 900 are located. The straight section 925 or scalloped cutouts may be used with a different tool for alternatively driving main body 900. Such a tool, however, may not be able to also drive set screw 1000.

Figure 38:
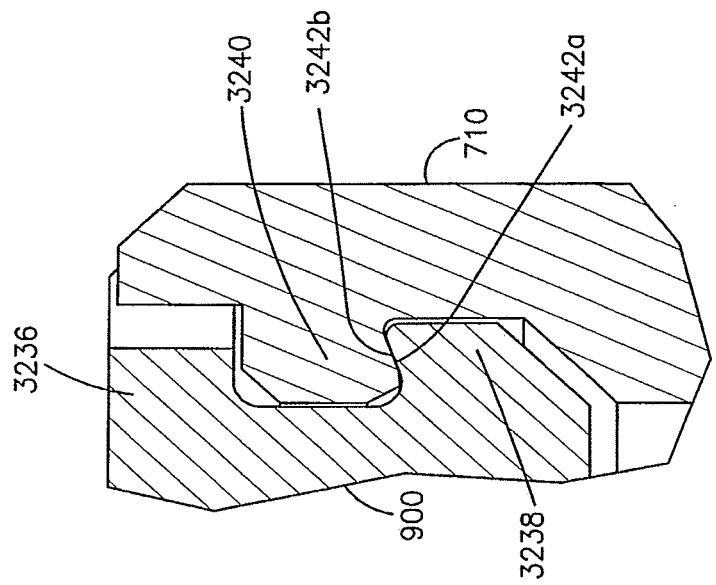
Figure 37:
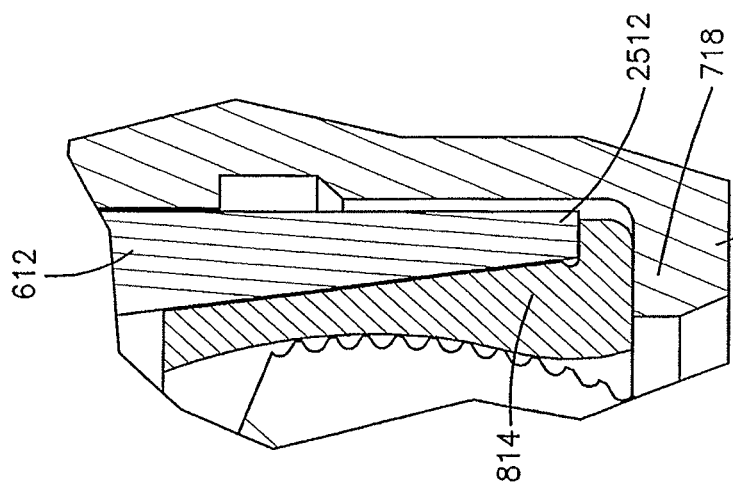

FIGS. 34-38 show locking cap 102 inserted and closed in anchor head 104, and set screw 1000 driven downward in anchor head 104 to lock rod 108 in place. As set screw 1000 is driven downward, it presses saddle 1100 against rod 108 to press the rod into the lower portion of the sleeve 612. Note the lack of space between saddle 1100 and rod 108 in FIG. 36. As the set screw is driven still further downward, the saddle presses the rod further downward which causes sleeve 612 to move downward, compressing collet 814 against the head of anchor member 106, locking the anchor member in place. More preferably, the sleeve 612 moves downward in the housing body 710 such that its interior tapered surface interacts with the tapered exterior surface of the collet 814 so that the resilient fingers of the collet are compressed inward to lock the anchor member into position so that the anchor member will be fixed to the body 710. Set screw 1000 may be driven downward until the bottom surface 2512 of sleeve 612 butts against the bottom inside surface 718 of housing 710, or until the bottom surface 2512 butts against the shoulder 828 of the collet (shown in FIG. 37). The anchor may also be configured so that the bottom surface 2512 of the sleeve may not butt against either the housing or collet when the anchor member is in the locked position. Additionally or alternatively, retention tabs 613*a,b* may butt against the respective lower edges 3015*a,b* of slots 715*a,b* upon completion of the anchor member locking process (as shown in FIG. 36). Note that the rod and anchor member locking process (i.e., the operation of moving of the set screw once it is free from the main body so that the saddle contacts the rod) has little, if any, effect on the relative closed positions of main body 900 and housing 710, as a comparison of FIGS. 32 and 38 shows.

A further illustrative method of using the bone fixation system utilizing the bone anchor 100 is described below. The bone anchor 100 including the anchor member and assembled body (including the sleeve and collet but preferably without the locking cap) is attached to the bone. At this step, the anchor member 106 preferably may polyaxially rotate or angulate with respect to housing 710. The anchor member 106 may be provisionally locked with respect to the housing 710 by applying a force to move sleeve 612 down toward the bottom opening 415 to compress the collet 814 against the head 717 to prevent movement of the anchor member relative to the housing 710. This provisional locking may be performed before the spinal rod is placed in the housing, or thereafter, and may be performed before the locking cap is attached to the housing or the spinal rod is clamped into the housing. In one method, the spinal rod may be placed in the sleeve and used to apply pressure on the sleeve to lock the anchor member to the housing before and independent of locking the spinal rod. With the anchor member locked in the housing 710, the spinal rod may be moved in the housing 710 (translated, rotated) or removed therefrom. The spinal rod may thereafter be clamped to the housing by using the locking cap 102 as described above.

Note that the locking cap is not limited to use in polyaxial bone anchors. FIGS. 39 and 40 show alternative bone anchors that can employ the locking cap of FIGS. 7 and 9-11. Bone anchor 3900 is an example of a monoaxial bone anchor having anchor member 3906. Bone anchor 4000 has anchor member 4006, which is an example of a hook which may engage the spinous process, a lamina, or other bone.

Figure 3:
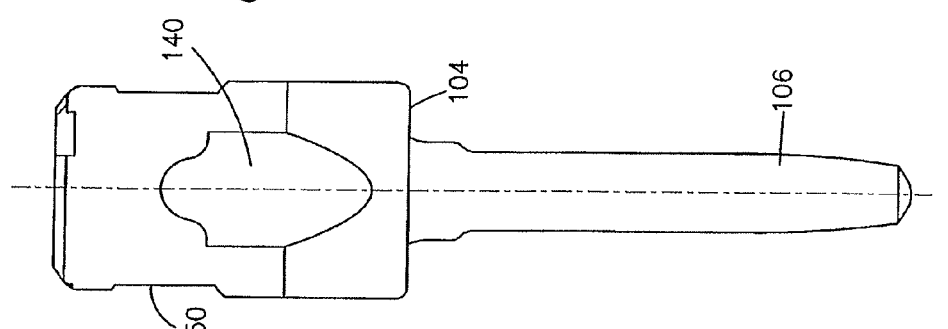
Figure 2:
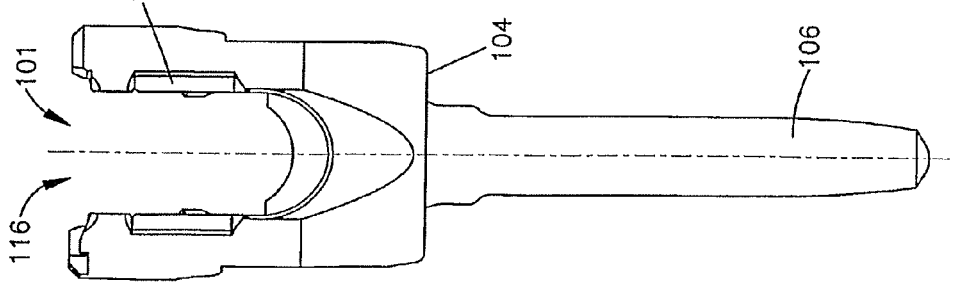

FIGS. 2 and 3 illustrate tool engaging surfaces 140 and 150 on the exterior of anchor head 104 that may be used with holding and manipulation instruments to assist in the implantation process.

A first illustrative method of fixation of the spine will be described. The method described below may be performed using any of the bone anchors described above, or any other bone anchors known in the art, although the polyaxial and monoaxial bone anchors described above are preferred. The method generally includes attaching a first bone anchor 100 to a vertebrae, preferably attaching a second bone anchor 100 to another vertebra, and securing a spinal rod to the first and second bone anchors 100 to align the vertebrae. This may be accomplished, for example, by inserting anchor member 106 of first bone anchor 100 into a first vertebra. The second bone anchor 100 may alternatively be implanted into one or more vertebrae in other regions of the spine (i.e., the cervical, thoracic, or lumbar regions).

In order to insert anchor member 106 into the vertebra, it may be necessary to insert anchor member 106 at an orientation of between about 0° and about 25° medially or laterally, and more preferably between about 0° and about 15° medially or laterally. Additionally or alternatively, it may be necessary to insert anchor member 106 at an orientation of between about 30° and about 50° upward, and between about 30° and about 40° upward. The polyaxial bone anchors described above may be configured and dimensioned to provide the necessary medial or lateral and/or upward angulation, although the present method is not limited to the structures of polyaxial bone anchors described herein.

Prior to inserting anchor member 106, drilling and/or tapping a hole into the vertebra may be desirable. In the case where the hole is tapped, it may be preferable not to tap the anterior cortex of the vertebra. Anchor head 104 and curved head 717 preferably may be preassembled before anchor member 106 is inserted into the vertebrae. Alternatively, once anchor member 106 has been fully inserted into the first vertebrae, anchor head 104 may be snapped onto the curved head 717 of anchor member 106.

Second polyaxial anchor 100 is preferably attached to an adjacent or other vertebra, for example, by threading anchor member 106 (which in this case is a screw) into the vertebra. Alternatively, second polyaxial anchor 100 may be attached to other vertebrae including those in the cervical, thoracic, or lumbar regions. Once the second polyaxial anchor is implanted, the first and second anchor heads 104 may be rotated to align their respective rod-receiving channels so that a spinal rod 108 may be inserted therein. Once the vertebrae have been repositioned to correct the deformity at hand, respective locking caps 102 of first and second polyaxial bone anchors 100 may be tightened to secure spinal rod 108 to the first and second polyaxial bone anchors 100, and to fix the angular positions of the anchor heads 104 with respect to the anchor members 106, thus forming a substantially rigid construct.

Alternatively, one end of spinal rod 108 can be inserted into one of anchor heads 104, and spinal rod 108 manipulated to reposition the vertebral bodies. Then the other end of the spinal rod 108 can be inserted into the other of anchor heads 104 and then spinal rod 108 fixed in position. The first end of spinal rod 108 may be fixed in one of anchor heads 104 with the locking cap before spinal rod 108 is manipulated to reposition the vertebral bodies. In yet another embodiment of this method, bone anchors 100 may be inserted into the spine as described above, both ends of spinal rod 108 may be inserted into anchors 100, and one end of the spinal rod fixed or secured into the anchor 100 and a distraction or compression force applied to move the polyaxial anchor along spinal rod 108 to apply either a distraction or compression force, and thereafter fixing the second end of spinal rod 108 into the bone anchor.

Once the first and second polyaxial anchors 100 have been implanted, their anchor heads 104 may rotated to align their respective rod-receiving channels so that a spinal rod 108 may be inserted therein. Once the vertebrae have been repositioned to correct the deformity at hand, the locking caps may be tightened to secure spinal rod 108 to first and second polyaxial anchors 100, and to fix the angular positions of the anchor heads 104 with respect to anchor member 106, thus forming a substantially rigid construct.

While it is apparent that the illustrative embodiments of the invention disclosed herein fulfill the objectives stated above, it will be appreciated that numerous modifications and other embodiments may be devised by those skilled in the art. Features and structures, such as, for example, the locking cap ca be used singularly or in combination with other features and structures. Therefore, it will be understood that the appended claims are intended to cover all such modifications and embodiments which come within the spirit and scope of the invention.

What is claimed is:
1. A bone anchor for attaching a fixation element to a bone, comprising:
an anchor member for attachment to the bone;
an anchor head having a proximal portion and a distal portion, the anchor head being coupled to the anchor member proximate the distal portion, the anchor head forming a hollow interior and having a generally U-shaped channel in the proximal portion for receiving the fixation element, the U-shaped channel being defined by opposed arms; and
a locking cap removably and non-threadably mountable to the proximal portion of the anchor head, the locking cap comprising:
a main body;
a set screw threadably attached to the main body to engage and clamp the fixation element to the anchor head; and
first and second tabs extending radially outward from the main body, each of the first and second tabs having at least a proximal-facing surface, a distal-facing surface, a radially-outward-facing surface, and an abutment surface extending between the proximal-facing surface, the distal-facing surface, and the radially-outward-facing surface;

wherein the locking cap is mountable to the proximal portion of the anchor head by rotating the locking cap with respect to the anchor head until the first and second tabs are positioned in corresponding first and second recesses formed in the arms of the anchor head such that the abutment surfaces of the first and second tabs abut retention surfaces of the first and second recesses, thereby preventing further rotation of the main body relative to the anchor head.

2. The bone anchor of claim 1, wherein the main body of the locking cap includes oppositely positioned straight surfaces engageable by a tool to rotate the main body relative to the anchor head.

3. The bone anchor of claim 1, wherein the set screw is preloaded in the main body such that rotation of the set screw causes the main body to rotate.

4. The bone anchor of claim 1, wherein the main body comprises screw threads on an internal surface for engaging screw threads on the set screw, and the set screw comprises a flared portion at the bottom end to engage a bottom end of the screw threads on the main body.

5. The bone anchor of claim 1, wherein at least a portion of the proximal-facing surfaces of the first and second tabs are ramped.

6. The bone anchor of claim 1, wherein the locking cap is movable between an open position and a closed position by rotating the locking cap about 90 degrees with respect to the anchor head.

7. The bone anchor of claim 1, wherein the height of first and second tabs is substantially equal to the height of the retention surfaces.

8. A bone anchor assembly, comprising:
a bone anchor having a threaded portion and a head portion;
an anchor head that receives the head portion of the bone anchor, the anchor head including a U-shaped recess configured to receive a spinal rod, the U-shaped recess being defined by opposed arms; and
a locking cap non-threadably mountable to the anchor head, the locking cap comprising:
a main body having a set screw disposed therein, the set screw being threadably attached to the main body; and
first and second tabs extending radially outward from the main body;
wherein the locking cap is positionable within the anchor head in at least an open configuration in which the first and second tabs are aligned with the U-shaped recess of the anchor head and a closed configuration in which the first and second tabs are disposed in corresponding first and second recesses formed in the arms of the anchor head and in which engagement between the tabs and the recesses resists rotation of the locking cap relative to the anchor head.

9. The bone anchor assembly of claim 8, wherein the main body of the locking cap includes oppositely positioned straight surfaces engageable by a tool to rotate the main body relative to the anchor head.

10. The bone anchor assembly of claim 8, wherein the set screw is preloaded in the main body such that rotation of the set screw causes the main body to rotate.

11. The bone anchor assembly of claim 8, wherein the main body comprises screw threads on an internal surface for engaging screw threads on the set screw, and the set screw comprises a flared portion at the bottom end to engage a bottom end of the screw threads on the main body.

12. The bone anchor assembly of claim 8, wherein the first and second tabs include a proximal-facing surface, at least a portion of the proximal facing-surface being ramped.

13. The bone anchor assembly of claim 8, wherein the locking cap is movable between the open configuration and the closed configuration by rotating the locking cap about 90 degrees with respect to the anchor head.

14. The bone anchor assembly of claim 8, wherein the height of first and second tabs is substantially equal to the height of the first and second recesses.

15. A bone anchor assembly, comprising:
a bone anchor having a threaded portion and a head portion;
an anchor head having a distal portion in which the head portion of the bone anchor is received and a proximal portion in which a U-shaped recess for receiving a spinal rod is formed, the U-shaped recess being defined by opposed arms; and
a locking cap non-threadably mountable to the proximal portion of the anchor head, the locking cap comprising:
a main body having a set screw disposed therein, the set screw being threadably attached to the main body; and
first and second tabs extending radially outward from the main body;
wherein the locking cap is mountable to the anchor head by rotating the main body relative to the anchor head to position the first and second tabs within corresponding first and second recesses formed in the arms of the anchor head until the first and second recesses prevent further rotation of the main body relative to the anchor head.

16. The bone anchor assembly of claim 15, wherein the main body of the locking cap includes oppositely positioned straight surfaces engageable by a tool to rotate the main body relative to the anchor head.

17. The bone anchor assembly of claim 15, wherein the set screw is preloaded in the main body such that rotation of the set screw causes the main body to rotate.

18. The bone anchor assembly of claim 15, wherein the main body comprises screw threads on an internal surface for engaging screw threads on the set screw, and the set screw comprises a flared portion at the bottom end to engage a bottom end of the screw threads on the main body.

19. The bone anchor assembly of claim 15, wherein the first and second tabs include a proximal-facing surface, at least a portion of the proximal facing-surface being ramped.

20. The bone anchor assembly of claim 15, wherein the locking cap is movable between an open configuration and a closed configuration by rotating the locking cap about 90 degrees with respect to the anchor head.

* * * * *